(12) United States Patent
Silkaitis et al.

(10) Patent No.: US 10,434,246 B2
(45) Date of Patent: Oct. 8, 2019

(54) MEDICATION MANAGEMENT SYSTEM

(71) Applicant: ICU Medical, Inc., San Clemente, CA (US)

(72) Inventors: Raymond P. Silkaitis, Thousand Oaks, CA (US); Geoffrey N. Holland, Ashland, OR (US); Patrick B. Keely, Tacoma, WA (US); Jeff Pelletier, Knoxville, TN (US)

(73) Assignee: ICU Medical, Inc., San Clemente, CA (US)

( * ) Notice: Subject to any disclaimer, the term of this patent is extended or adjusted under 35 U.S.C. 154(b) by 785 days.

(21) Appl. No.: 14/841,008

(22) Filed: Aug. 31, 2015

(65) Prior Publication Data

US 2016/0051751 A1    Feb. 25, 2016

Related U.S. Application Data

(63) Continuation of application No. 10/783,640, filed on Feb. 20, 2004, now Pat. No. 9,123,077.

(Continued)

(51) Int. Cl.
*A61M 5/142* (2006.01)
*G06Q 50/00* (2012.01)
(Continued)

(52) U.S. Cl.
CPC ......... *A61M 5/142* (2013.01); *G06F 19/3468* (2013.01); *G06Q 50/00* (2013.01); *G06Q 50/22* (2013.01); *A61M 2005/14208* (2013.01)

(58) Field of Classification Search
CPC ................. G06Q 50/22–50/24; G06F 19/3418
See application file for complete search history.

(56) References Cited

U.S. PATENT DOCUMENTS

| 4,024,864 A | 5/1977 | Davies et al. |
| 4,055,175 A | 10/1977 | Clemens et al. |

(Continued)

FOREIGN PATENT DOCUMENTS

| CA | 2 060 151 | 8/1997 |
| CA | 2 125 300 | 10/1999 |

(Continued)

OTHER PUBLICATIONS

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

(Continued)

*Primary Examiner* — Robert A Sorey
(74) *Attorney, Agent, or Firm* — Knobbe Martens Olson & Bear, LLP

(57) ABSTRACT

A medication management system (MMS) includes a medication management unit (MMU) associated with a medical device. The MMU downloads a medication order to the medical device only if information from a first input matches information from a second input. The medical device receives delivery information only from the MMU. The medication order is performed only after delivery data validation. The MMU also determines drug-drug incompatibility. The MMU can modulate (start, stop, and dynamically adjust) medication order performance. The medical device wirelessly receives a patient ID to automatically associate with the patient. During delivery, the medical device caches an updated drug library to replace an existing one. The medical device displays a patient picture for validation. The MMU evaluates the performance of medical devices and caregivers based medical device feedback. The MMU (Continued)

adjusts the output of medical device information conveyed to a caregiver.

6 Claims, 25 Drawing Sheets

Related U.S. Application Data

(60) Provisional application No. 60/527,583, filed on Dec. 5, 2003, provisional application No. 60/509,404, filed on Oct. 7, 2003.

(51) Int. Cl.
*G06Q 50/22* (2018.01)
*G06F 19/00* (2018.01)

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |

(56) References Cited

U.S. PATENT DOCUMENTS

| | | |
|---|---|---|
| 5,630,710 A | 5/1997 | Tune et al. |
| 5,636,044 A | 6/1997 | Yuan et al. |
| 5,507,288 A | 7/1997 | Bocker et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | De La Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,032,155 A | 2/2000 | De La Huerga |
| 6,032,676 A | 3/2000 | Moore |
| 6,073,106 A | 6/2000 | Rozen et al. |
| 6,104,295 A | 8/2000 | Gaisser et al. |
| 6,112,182 A | 8/2000 | Akers et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | De La Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |

(56) References Cited

U.S. PATENT DOCUMENTS

| | | |
|---|---|---|
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter et al. |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 * | 12/2005 | Surwit ............. G06F 19/3418 705/2 |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | De La Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,343,224 B2 | 11/2008 | DiGianfilippo et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |

(56) References Cited

U.S. PATENT DOCUMENTS

| | | |
|---|---|---|
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,078,983 B2 | 12/2011 | Davis et al. |
| 8,082,018 B2 | 12/2011 | Duchon et al. |
| 8,082,312 B2 | 12/2011 | Chan et al. |
| 8,147,448 B2 | 4/2012 | Sundar et al. |
| 8,149,131 B2 | 4/2012 | Blornquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,577,692 B2 | 11/2013 | Silkaitis et al. |
| 8,579,884 B2 | 11/2013 | Lanier et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,922,330 B2 | 12/2014 | Moberg et al. |
| 8,936,565 B2 | 1/2015 | Chawla |
| 8,952,794 B2 | 2/2015 | Bloomquist et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,381,296 B2 | 7/2016 | Arrizza et al. |
| 9,393,362 B2 | 7/2016 | Cozmi et al. |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,724,470 B2 | 8/2017 | Day et al. |
| 9,764,082 B2 | 9/2017 | Day et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 2001/0013854 A1 | 8/2001 | Ogoro |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |

(56) References Cited

U.S. PATENT DOCUMENTS

| | | |
|---|---|---|
| 2002/0029776 A1 | 3/2002 | Blomquist |
| 2002/0032583 A1 | 3/2002 | Joao |
| 2002/0038392 A1* | 3/2002 | De La Huerga .. A61M 5/14212 710/8 |
| 2002/0040208 A1 | 4/2002 | Flaherty et al. |
| 2002/0040282 A1 | 4/2002 | Bailey et al. |
| 2002/0077852 A1 | 6/2002 | Ford et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1* | 10/2002 | Bristol .................. G06Q 50/22 705/2 |
| 2002/0152239 A1 | 10/2002 | Bautista-Lloyd et al. |
| 2002/0169636 A1 | 11/2002 | Eggers et al. |
| 2002/0194329 A1 | 12/2002 | Ailing |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1* | 1/2003 | Gallant .................. A61G 7/00 5/600 |
| 2003/0025602 A1 | 2/2003 | Medema |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0114836 A1 | 6/2003 | Estes |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1* | 5/2005 | Oshita .................. A61M 1/14 705/3 |
| 2005/0102669 A1 | 5/2005 | Marney et al. |
| 2005/0107923 A1 | 5/2005 | Vanderveen |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0273059 A1 | 12/2005 | Mernoe et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |

(56) References Cited

U.S. PATENT DOCUMENTS

| | | |
|---|---|---|
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213598 A1 | 9/2007 | Howard et al. |
| 2007/0213657 A1 | 9/2007 | Jennewine et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0200870 A1 | 8/2008 | Palmroos et al. |
| 2008/0214919 A1 | 9/2008 | Harmon et al. |
| 2008/0243055 A1 | 10/2008 | Fathallah et al. |
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |

(56) References Cited

U.S. PATENT DOCUMENTS

| | | |
|---|---|---|
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121415 A1 | 5/2010 | Skelton et al. |
| 2010/0121654 A1 | 5/2010 | Portnoy et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0175728 A1 | 7/2011 | Baker, Jr. |
| 2011/0178462 A1 | 7/2011 | Moberg et al. |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0130308 A1 | 5/2012 | Silkaitis et al. |
| 2012/0143116 A1 | 6/2012 | Ware et al. |
| 2012/0150556 A1 | 6/2012 | Galasso et al. |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012880 A1 | 1/2013 | Blomquist |
| 2013/0015980 A1 | 1/2013 | Evans et al. |
| 2013/0035633 A1 | 2/2013 | Chawla |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0085689 A1 | 4/2013 | Sur et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0158504 A1 | 6/2013 | Ruchti et al. |
| 2013/0167245 A1 | 6/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2014/0039446 A1 | 2/2014 | Day |
| 2014/0257251 A1 | 9/2014 | Bush et al. |
| 2014/0266790 A1 | 9/2014 | Al-Ali et al. |
| 2014/0269643 A1 | 9/2014 | Sun |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2015/0005935 A1 | 1/2015 | Bae et al. |
| 2015/0058044 A1 | 2/2015 | Butler et al. |
| 2015/0066531 A1 | 3/2015 | Jacobson et al. |
| 2015/0100038 A1 | 4/2015 | McCann et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0379237 A1 | 12/2015 | Mills et al. |
| 2016/0051749 A1 | 2/2016 | Istoc |
| 2016/0103960 A1 | 4/2016 | Hume et al. |
| 2016/0228633 A1 | 8/2016 | Welsch et al. |
| 2016/0350513 A1 | 12/2016 | Jacobson et al. |
| 2017/0024534 A1 | 1/2017 | Arrizza et al. |
| 2017/0246388 A1 | 8/2017 | Kohlbrecher |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0331735 A1 | 11/2017 | Jha et al. |
| 2018/0008772 A1 | 1/2018 | Wehba et al. |
| 2018/0028742 A1 | 2/2018 | Day et al. |
| 2018/0043094 A1 | 2/2018 | Day et al. |

FOREIGN PATENT DOCUMENTS

| | | |
|---|---|---|
| DE | 31 12 762 | 1/1983 |
| DE | 34 35 647 | 7/1985 |
| DE | 19932147 | 7/1999 |
| DE | 198 44 252 | 3/2000 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0683465 | 11/1995 |
| EP | 0880936 | 12/1998 |
| EP | 1 157 711 | 11/2001 |
| EP | 1 174 817 | 1/2002 |
| EP | 0 664 102 | 4/2002 |
| EP | 1197178 | 4/2002 |
| EP | 0 830 775 | 8/2002 |

(56) References Cited

FOREIGN PATENT DOCUMENTS

| | | |
|---|---|---|
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2717919 | 3/1994 |
| GB | 2 285 135 | 6/1995 |
| JP | 04-161139 | 6/1992 |
| JP | H07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-511287 | 5/2007 |
| JP | 2007-518479 | 7/2007 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2012-070991 | 4/2012 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | 96/08755 | 3/1996 |
| WO | WO 96/025186 | 8/1996 |
| WO | 98/12670 | 3/1998 |
| WO | 98/19263 | 5/1998 |
| WO | 99/51003 | 10/1999 |
| WO | WO 00/013580 | 3/2000 |
| WO | WO 00/053243 | 9/2000 |
| WO | 01/14974 | 3/2001 |
| WO | 01/33484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2017/176928 | 10/2017 |

OTHER PUBLICATIONS

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. http://corp.bbraun.ee/Extranet/infusioonipumbad/Kasutusjuhendid/Vanad/Kasutusjuhend-Infusomat_Space(vers688J.inglise_k).pdf.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris - Service_Manual.pdf.

(56) References Cited

OTHER PUBLICATIONS

"CareAware® Infusion Management", Cerner Store, as printed May 12, 2011, pp. 3, https://store.cerner.com/items/7.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_interoperability.pdf%3fnodeid%3d8508574%26vernum%3d-2, pp. 2.
Felleiter et al., "Data Processing in Prehospital Emergency Medicine", International journal of Clinical Monitoring and Computing, Feb. 1995, vol. 12, No. 1, pp. 37-41.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Micrel Medical Devices, "MP Daily +" http://web.archive.org/web/20130803235715/http://www.micrelmed.com/index.aspx?productid-9 as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.

(56) References Cited

OTHER PUBLICATIONS

Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph. D. "Computer Control of the Infusion of Vasocactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"SIGMA Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://:www.thomasland.com/hpi4209-832.pdf.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodder, Lisa, "A Center Keeps Medicine in Right Hands", Dec. 4, 1999, pp. 1-2.
Stitt, F.W., "The Problem-Oriented Medical Synopsis: a Patient-Centered Clinical Information System", Proceedings of the Annual Symposium on Computer Application in Medical Care, 1994, pp. 88-92.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Preliminary Report on Patentability and Written Opinion received in PCT Application No. PCT/US2004/037900, dated May 15, 2006 in 5 pages.
International Search Report and Written Opinion received in PCT Application No. PCT/US2004/033409, dated Sep. 13, 2015 in 11 pages.
General-Purpose Infusion Pumps, Health Devices, Oct. 1, 2002, pp. 353-387, vol. 31, No. 10, ECRI Institute.
Eskew J. A. et al, Using Innovative Technologies to Set New Safety Standards for the Infusion of Intravenous Medications, Hospital Pharmacy, Nov. 1, 2002, pp. 1179-1189, vol. 37, No. 11, Lippincott, Philadelphia, PA.

(56) References Cited

OTHER PUBLICATIONS

Stokowski et al, Using Technology to Improve Medication Safety in the Newborn Intensive Care Unit, Advances in Neonatal Care, Dec. 1, 2001, pp. 70-83, vol. 1, No. 2, W. B. Saunders.
European Search Report dated Nov. 23, 2010 for EP 10 18 2287.
International Search Report dated Dec. 3, 2010 for EP 10182326.
Microsoft, "Computer Dictionary, Third Edition", Microsoft Press, 1997, pp. 430 and 506.
Yen-Cheng Chen et al, "Enabling location-based services on wireless LANs", Networks, 2003. ICON2003. The 11th IEEE International Conference on Sep. 28-Oct. 1, 2003, Piskataway, NJ, USA, Sep. 28, 2003, pp. 567-572.
"Infusion Pump", Wikipedia.org, https://web.archive.org/web/20140703024932/https://en.wikipedia.org/wiki/infusion_pump, as last modified Mar. 27, 2014, pp. 3.
International Preliminary Report on Patentability and Written Opinion received in PCT Application No. PCT/US2004/033409, dated Apr. 10, 2006 in 7 pages.
Gabel et al., "Camp: A Common API for Measuring Performance", 21st Large Installations System Administration Conference (LISA '07), 2007, pp. 49-61.
Sutton et al., "The Syntax and Semantics of the PROforma Guideline Modeling Language", Journal of the American Medical Informatics Association, Sep./Oct. 2003, vol. 10, No. 5, pp. 433-443.

\* cited by examiner

143B

:PDAAPP01_2004

File   Zoom   Tools   Help

Caregiver Task List

Name: Holland, Neil

NS 1000 mL

|  | Ordered | Pump |
|---|---|---|
| Perform Date | 02-20-2004 ▼ | |
| Perform Time | 4:45:00 PM ⬍ | |
| Bag # | – | |
| Volume (mL) | 1000 | |
| Rate (mL / hr) | 10 | |
| Site | ▼ | |
| Backpress | – | |

Scan Pump Channel

[Cancel]                    [Complete]

FIG. 11

:PDAAPP01_2004

File   Zoom   Tools   Help

Caregiver Task List

Name: Holland, Neil

NS 1000 mL

|  | Ordered | Pump |
|---|---|---|
| Perform Date | 02-20-2004 ▼ | |
| Perform Time | 4:45:00 PM ↕ | |
| Bag # | – | |
| Volume (mL) | 1000 | 1000.00 |
| Rate (mL/hr) | 10 | 10.00 |
| Site | ▼ | |
| Backpress | – | 1.00 |

Pump Running

[Cancel]   [Complete]

191A → (NS 1000 mL)
191C → Cancel
191B → Complete

FIG. 16

MEDICATION MANAGEMENT SYSTEM

BACKGROUND OF THE INVENTION

The present invention relates to the field of delivering medication to patients, more particularly to an integrated system for maximizing patient safety and caregiver productivity for medication delivery.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. However, modern medical devices, including medical pumps, can be complicated and time-consuming for caregivers to program. Medical facilities struggle to provide appropriate caregiver staffing levels and training while holding down the cost of medical care. Human errors in pump programming and other medication errors can have adverse or even deadly consequences for the patient.

Therefore, a principal object of this invention is to provide an integrated medication management system that reduces the risks of medication error and improves patient safety.

A further object of the invention is to provide a medication management system that improves caregiver productivity.

Another object of the invention is to provide a medication management system that improves the accuracy of the medication delivery process by eliminating labor-intensive tasks that can lead to human errors.

A still further object of the invention is to provide a medication management system that relies on an electronically-transmitted medication order and machine readable indicia on the drug container, patient, and medication delivery device to insure the "five rights" of medication management, i.e., that the right medication is delivered to the right patient through the right route in the right dosage at the right time.

Another object of the invention is to provide the caregiver with a pass code or machine-readable indicia to insure that only an authorized individual caregiver can initiate a medication order and that an authorized caregiver must confirm the medication order prior to its administration to the patient.

A still further object of the invention is to provide a medication management system wherein the medical device receives delivery information electronically only through a medication management unit.

Another object of the invention is to provide medication management system wherein the medical device is preprogrammed and executes the medication order only after a user has validated delivery data.

A still further object of the invention is to provide a medication management system wherein the physical location of a medical device can be determined and pinpointed based on the last access node used by the medical device.

Another object of the invention is to provide a medication management system for adjusting a patient-specific rule set based on new patient conditions and/or recent lab results.

A still further object of the invention is to provide a medication management system for determining drug-drug incompatibility between two medication orders for concurrent delivery (to the same patient at the same time) and/or in an unacceptably close time sequence.

Another object of the invention is to provide a medication management system for remotely sending an order or information to the medical device to modulate a planned or ongoing medication order and delivery thereof to the patient.

A still further object of the invention is to provide a medication management system for automatically associating a medical device with a patient based on wireless transmission of a patient ID to the medical device, thereby establishing a patient area network.

Another object of the invention is to provide a medication management system for caching an updated drug library at the medical device to replace an existing drug library, during execution of a medication order.

A still further object of the invention is to provide a medication management system for displaying a picture of the patient on a device within the system, such as at the medical device, for a caregiver to perform a visual validation of the right patient.

Another object of the invention is to provide a medication management system for evaluating the performance of multiple medical devices based on information from the multiple medical devices.

A still further object of the invention is to provide a medication management system for evaluating the performance of one or more caregivers based on information from multiple medical devices.

Another object of the invention is to provide a medication management system for adjusting medical device output conveyed to a caregiver based on multiple factors.

These and other objects will be apparent to those skilled in the art.

SUMMARY OF THE INVENTION

A medication management system includes a medication management unit (MMU) associated with a medical device for performing a prescribed medication order. The MMU compares medication order information from a first input means to machine readable delivery information from a second input means and downloads a medication order to the medical device only if the information from the first input means matches the information from the second input means. The medical device receives medication order information electronically only through the medication management unit (i.e., does not receive delivery information directly from the second input means). The MMU permits the medical device to perform the order only after a user has validated delivery data at the medical device.

The MMU determines the general physical location of a medical device based on the last access node used by the wireless connectivity capability in the medical device and an audible alarm can be activated to allow a user to pinpoint the physical location of the medical device more precisely.

Using expert clinical support decision rules, the MMU also determines drug-drug incompatibility between two medication orders for concurrent delivery (to the same patient at the same time) and/or in an unacceptably close time sequence through the same output IV line. Further, the MMU also adjusts patient-specific rule sets based on newly measured or observed patient conditions and/or recent lab results. Advantageously, warnings, alarms or alerts based on violations of these rules are provided as close as possible to the actual delivery time so that they are more meaningful, ripe for corrective action, and less likely to be ignored due to incomplete information.

Based on laboratory data or other newly received patient information, the MMU can modulate the medication order planned or currently being delivered. The MMU sends an order from the MMU to the medical device to modulate performance of the medication order. The patient and the medical device automatically associate with each other to form a patient area network based on wireless transmission of ID information. During execution of a medication order, the medical device caches an updated drug library in a cache memory and, upon occurrence of a triggering event, replaces an existing drug library in the primary memory of the device with the updated library. A picture of the patient is displayed at a device within the system, such as the medical device, for a caregiver to perform a visual validation of the right patient. The MMU evaluates the performance of multiple medical devices and one or more caregivers based on information communicated from the medical devices. The MMU adjusts medical device output conveyed to a caregiver based on multiple factors.

DESCRIPTION OF THE DRAWINGS

FIG. 11 is a screen shot of a delivery information input device displaying a medication order prescribed for a patient;

FIG. 16 is a screen shot of a delivery information input device for confirming correct delivery programming code data;

DETAILED DESCRIPTION OF THE PREFERRED EMBODIMENT

Figure 1:
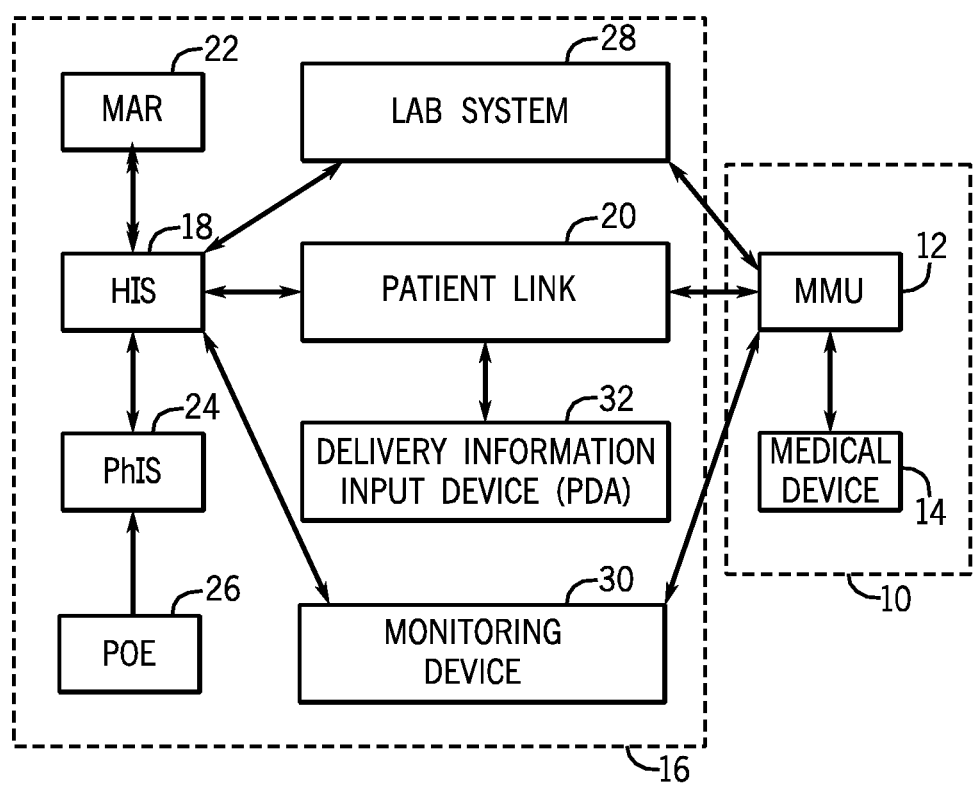
FIG. 1 is a schematic diagram of the medication management system including a medication management unit and a medical device, integrated with an information system, according to the present invention.

With reference to FIG. 1, the medication management system (MMS) 10 of the present invention includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. As discussed below, there can be a variety of information systems in a hospital environment. As shown in FIG. 1, the MMU 12 communicates to a hospital information system (HIS) 18 via a caching mechanism 20 that is part of the hospital environment 16.

It will be understood by those of skill in art that the caching mechanism 20 is primarily a pass through device for facilitating communication with the HIS 18 and its functions can be eliminated or incorporated into the MMU 12 and/or the medical device 14 and/or the HIS 18 and/or other information systems or components within the hospital environment 16. The Caching Mechanism 20 provides temporary storage of hospital information data separate from the HIS 18, the medication administration record system (MAR) 22, pharmacy information system (PhIS) 24, physician order entry (POE) 26, and/or Lab System 28. The Caching Mechanism 20 provides information storage accessible to the Medication Management System 10 to support scenarios where direct access to data within the hospital environment 16 is not available or not desired. For example, the caching mechanism 20 provides continued flow of information in and out of the MMU 12 in instances where the HIS 18 down or the connectivity between the MMU 12 and the electronic network (not shown) is down. The caching mechanism 20 also provides improved response time to queries from the MMU 12 to the HIS 18, as direct queries to the HIS 18 are not consistently processed at the same speed and often require a longer period of time for the HIS 18 to process.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. For example, the lab system 28 sends lab results of blood work on a specific patient to the MMU 12, while the monitoring device 30 sends current and/or logged monitoring information such as heart rate to the MMU 12. As shown, the MMU 12 communicates directly to the lab system 28 and monitoring device 30. However, it will be understood to those of skill in art that the MMU 12 can communicate to the lab system 28 and monitoring device 30 indirectly via the HIS 18, the caching mechanism 20, the medical device 14 or some other intermediary device or system. This real-time or near delivery time patient-specific information is useful in adapting patient therapy because it may not have been available at the time the medication order was prescribed. As used herein, the term real-time denotes a response time with a latency of less than 3 seconds. The real-time digital communications between the MMU 12 and other interconnected devices and networks prevents errors in patient care before administration of medications to the patient, especially in the critical seconds just prior to the start of medication delivery.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
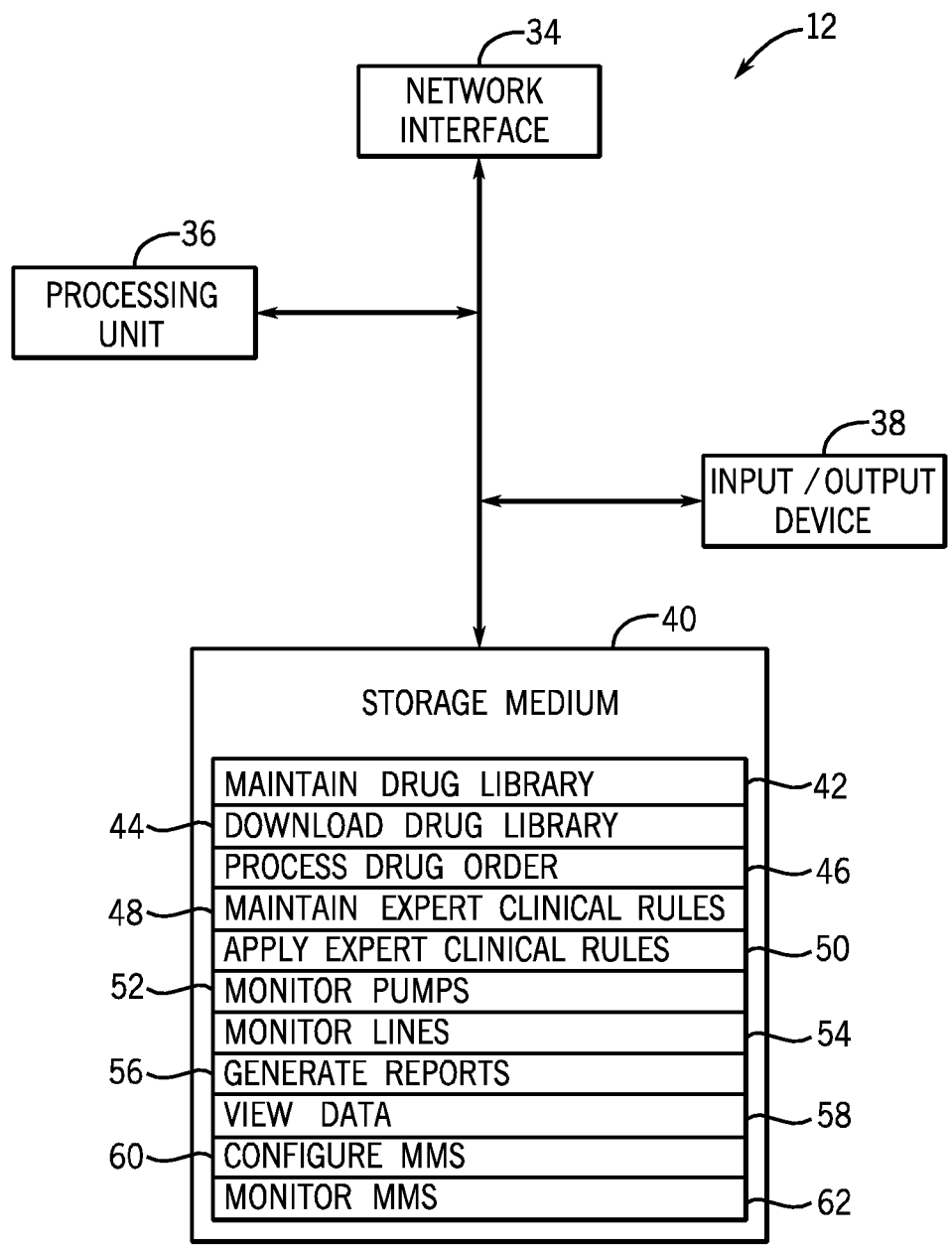
FIG. 2 is a schematic diagram of the medication management unit according to the invention.

With reference to FIG. 2, the medication management unit 12 includes a network interface 34 for connecting the MMU 12 to multiple components of a hospital environment 16, the medical device 14, and any other desired device or network. A processing unit 36 is included in MMU 12 and performs various operations described in greater detail below. A display/input device 38 communicates with the processing unit 36 and allows the user to receive output from processing unit 36 and/or input information into the processing unit 36. Those of ordinary skill in the art will appreciate that display/input device 38 may be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed in accordance with the present invention for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions that include blood chemistry values such as insulin/glucose, monitored data such as pulse and respiration, and clinician assessments such as pain or responsiveness. The Monitor Pumps 52 program acquires ongoing updates of status, events, and alarms transmitted both real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS 10 components and processing, and other aspects of day-to-day operations such as system start up, shut down, backup and restore.

Figure 3:
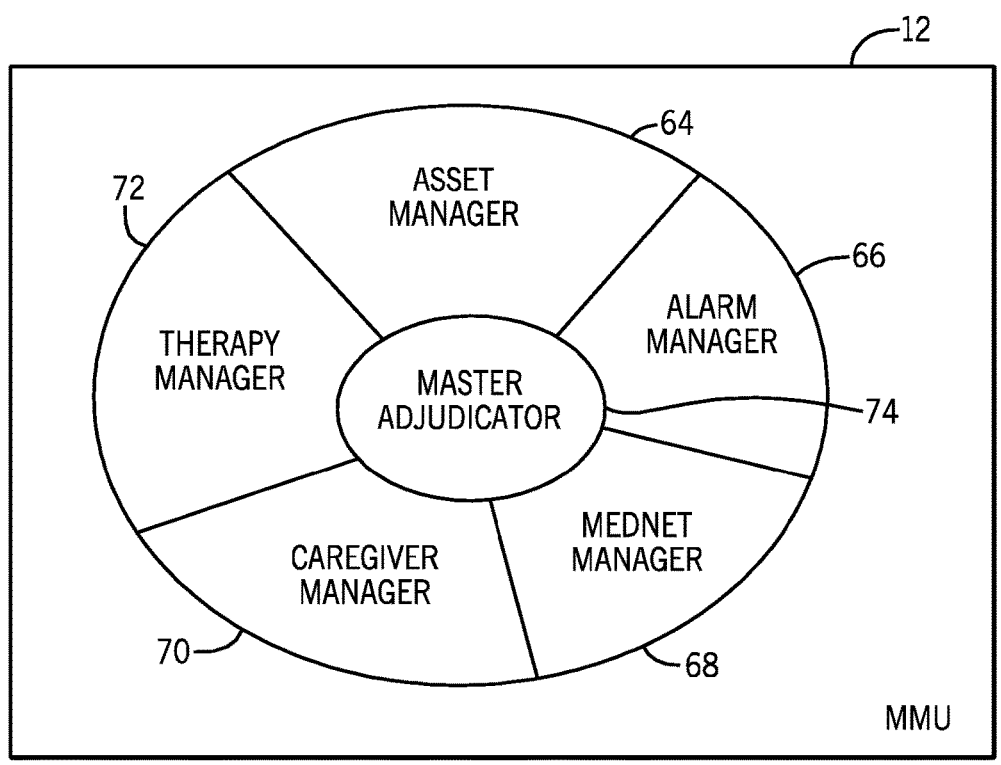
FIG. 3 is a schematic diagram illustrating some of the major functions performed by the medication management unit according to the invention.

With reference to FIG. 3, the various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, ABBOTT MEDNET™) 68, a caregiver manager 70, a therapy manager 72, and/or a clinical data manager 73. However, one of ordinary skill in the art will appreciate that additional or alternative hospital system managing units can be provided without departing from the present invention. Additionally, the MMU 12 includes a master adjudicator 74 between the separate interrelated hospital system managing units 64-73 of the MMU 12, to regulate the interaction between the separate management units.

Further, while the MMU 12 as described herein appears as a single device, there may be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 74 assigns redirected service requests to another server portion of the MMU 12, prioritizing each request and also ensuring that each request is processed.

With reference to FIGS. 2 and 3, the managing units 64-72 each include separate features and rules to govern their operation. For example the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the hospital system managing units 64-73 can be made in accordance with the present invention.

Figure 4:
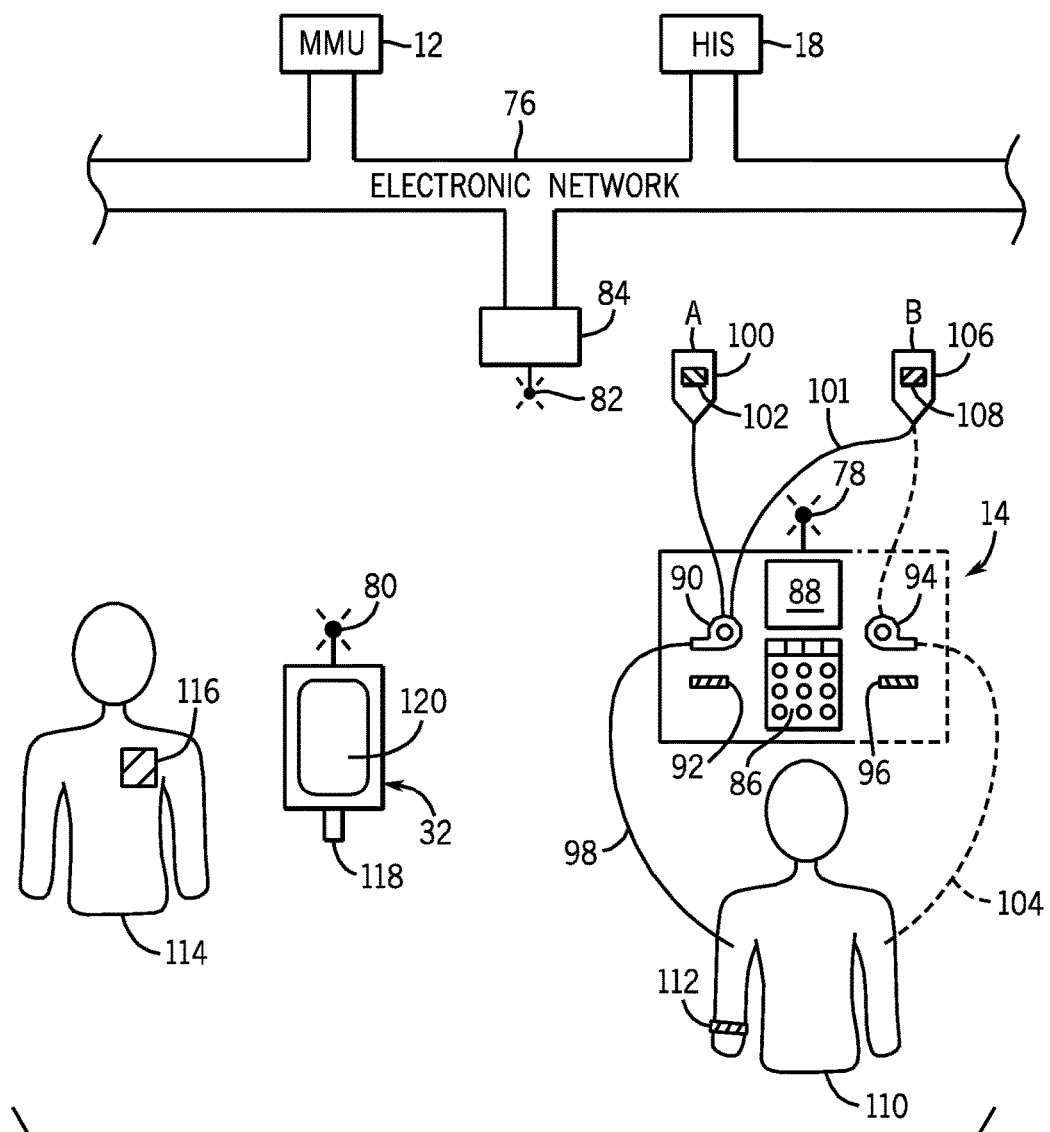
FIG. 4 is a pictorial schematic diagram of the medication management system and its interaction with medical devices and an information system in a hospital environment.

With reference to FIG. 4, an electronic network 76 connects the MMU 12, medical device 14, HIS 18, and input device 32 for electronic communication. The electronic network 76 can be a completely wireless network, a completely hard wired network, or some combination thereof. The medical device 14 and input device 32 are located in a treatment location 77. As shown, the medical device 14 and input device 32 are equipped with antennas 78 and 80, respectively. The antennae 78 and 80 provide for wireless communication to the electronic network 76 via an antenna 82 of access node 84 connected to the electronic network 76. Further details on the antenna 78 can be found in commonly assigned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

In the context of the present invention, the term "medical device" includes without limitation a device that acts upon a cassette, reservoir, vial, syringe, or tubing to convey medication or fluid to or from a patient (for example, an enteral pump, infusion pump, a patient controlled analgesia (PCA) or pain management medication pump, or a suction pump), a monitor for monitoring patient vital signs or other parameters, or a diagnostic device.

For the purpose of exemplary illustration only, the medical device 14 of FIG. 4 is disclosed as a cassette type infusion pump. The pump style medical device 14 includes a user interface means 86, display 88, first channel 90, and first channel machine readable indicator 92. A first IV line 98 has a conventional cassette 99A (not shown) that is inserted into the first channel 90, and includes a medication bag 100 with a machine readable indicator 102. A second IV line 101 is connected to an input port of the cassette 99A, and includes a medication bag 106 with a machine readable indicator 108. A single output IV line 98 is connected to an outlet port of the cassette 99A and connected to a patient 110 who has a machine readable indicator 112 on a wristband, ankle band, badge or similar article that includes patient-specific and or identifying information, including but not limited to patient ID, and demographics.

In an alternative embodiment illustrated by dashed lines in FIG. 4, the medical device 14 is a multi-channel pump having a first channel 90 with first channel machine readable indicator 92 and at least a second channel 94 with a second channel machine readable indicator 96. The line 101 from the medication bag 106 is eliminated and replaced by line 104 with a cassette 99B (not shown) inserted into the second channel 94 and an output line 104 extends from the cassette to the patient. The same type of cassette 99 (not shown) is inserted in the first channel 90. Additional details on such a multi-channel pump and cassette 99A can be found in commonly owned U.S. patent application Ser. No. 10/696,830 entitled MEDICAL DEVICE SYSTEM, which is incorporated by reference herein in its entirety.

Within a patient area network 113 (hereinafter, PAN 113), a caregiver 114 (if present) has a machine readable indicator 116 on a wristband, badge, or similar article and operates the input device 32. The input device 32 includes an input means 118 for reading the machine readable indicators 92, 96, 102, 108, 112, and 116. An input/output device 120 is included on the input device 32. The input/output device 120 allows the user to receive output from the input device 32 and/or input into the input device 32. Those of ordinary skill in the art will appreciate that display/input device 120 may be provided as a separate display device and a separate input device.

Figure 4A:
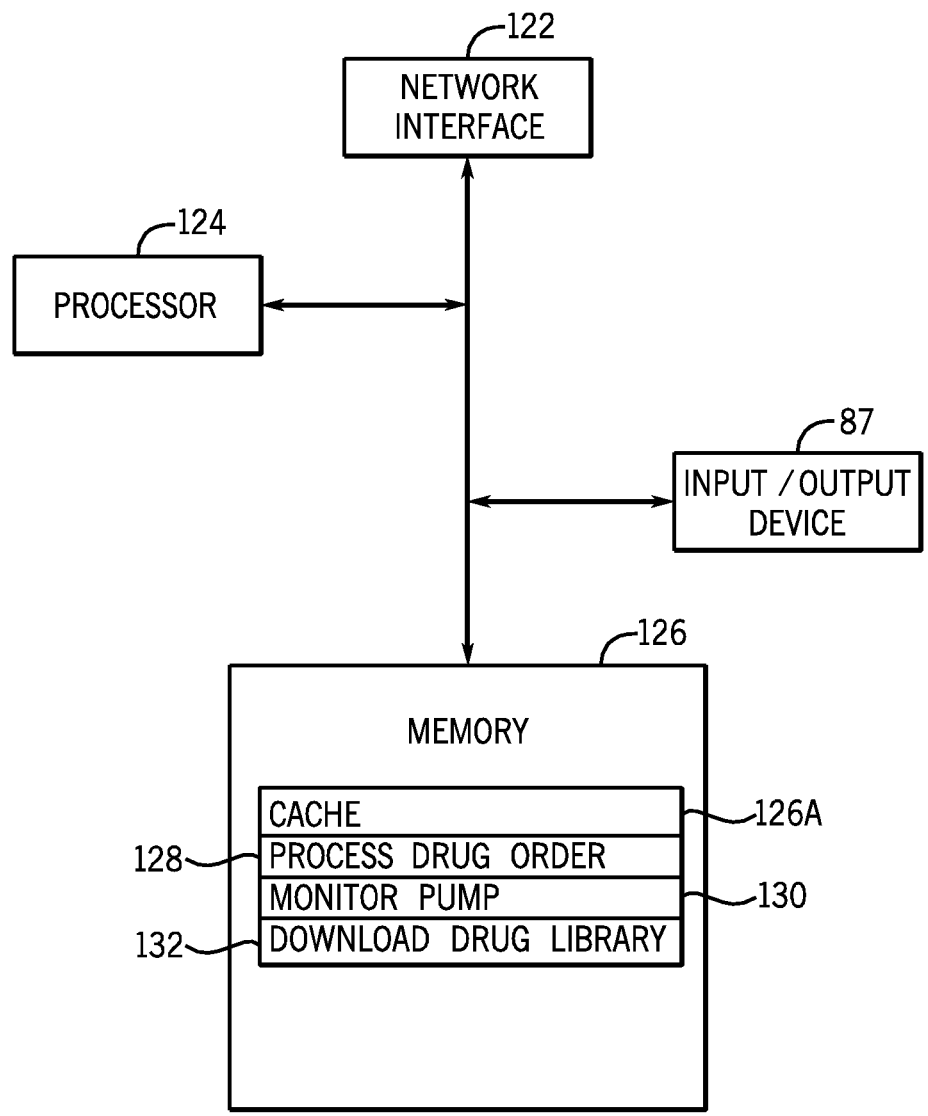
FIG. 4A is a schematic diagram of the medical device according to the invention.

With reference to FIG. 4A, the pump style medical device 14 includes a network interface 122 for connecting the medical device 14 to the electronic network 76. The network interface 122 operates the antenna 78 for wireless connection to the electronic network 76. A processor 124 is included in the medical device 14 and performs various operations described in greater detail below. The input/output device 87 (display 88 and user interface means 86) allows the user to receive output from the medical device 14 and/or input information into the medical device 14. Those of ordinary skill in the art will appreciate that input/output device 87 may be provided as a separate display device and a separate input device (as shown in FIG. 4, display 88 and user interface means 86) or combined into a touch screen for both input and output. A memory 126 communicates with the processor 124 and stores code and data necessary for the processor 124 to perform the functions of the medical device 14. More specifically, the memory 126 stores multiple programs formed in accordance with the present invention for various functions of the medical device 14 as is relates to the MMU 12 including the following programs: Process Drug Order 128, Monitor Pump 130, and Download Drug Library 132.

Figure 5:
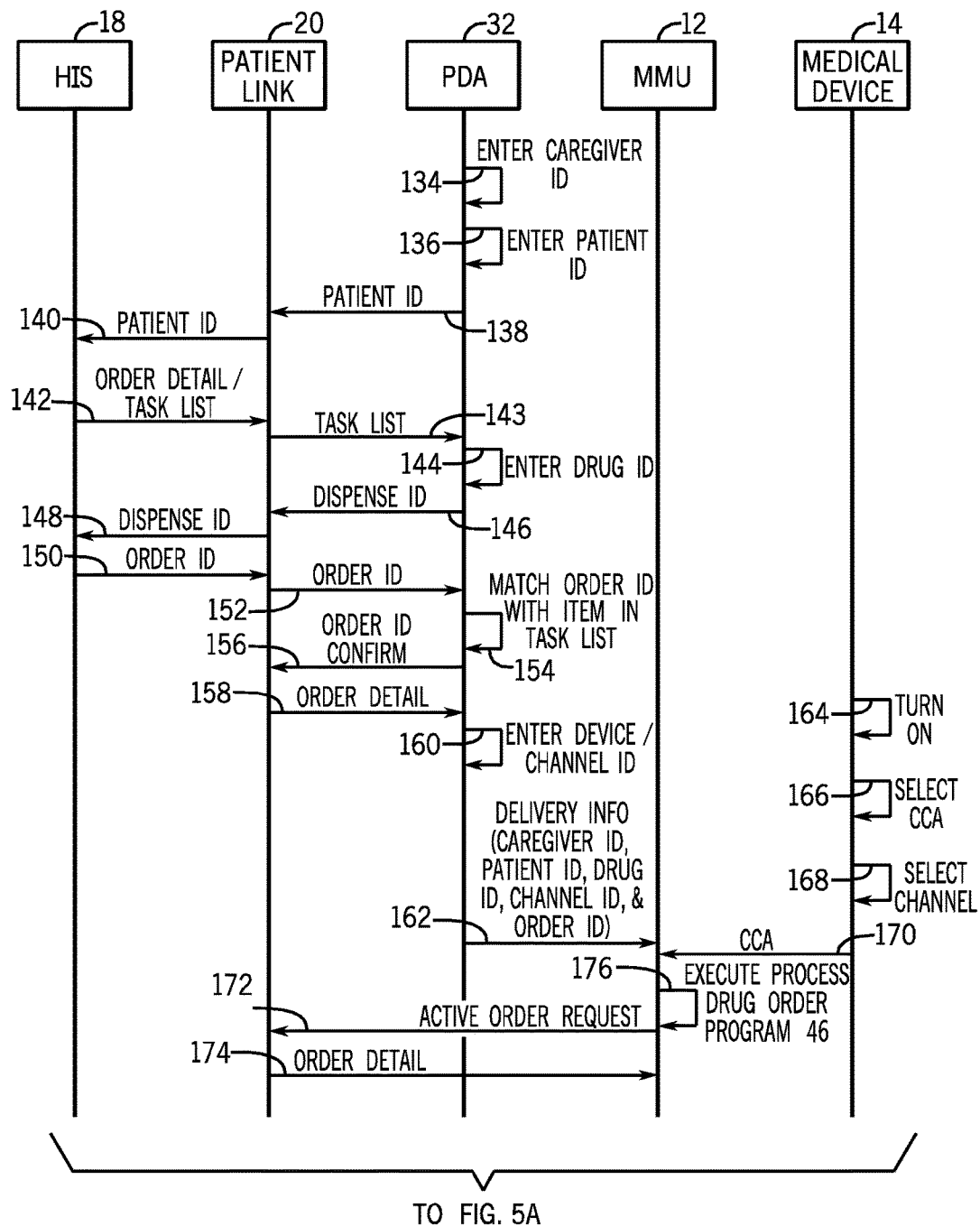
FIG. 5 is a partial flow chart of the medication management system processing a drug order through the medication management unit and medical device, and integrated with an information system according to the invention.
Figure 5A:
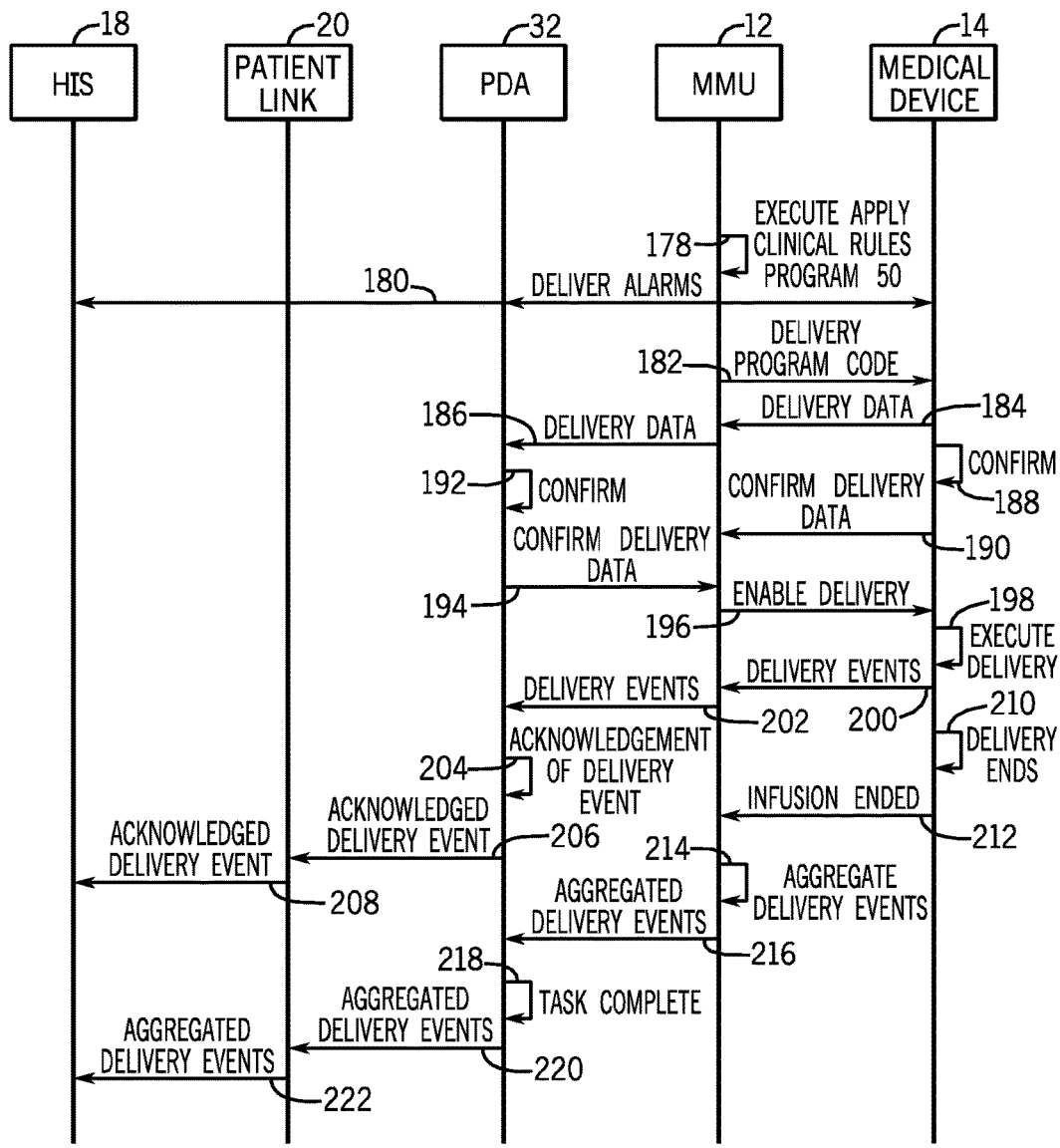
FIG. 5A is a continuation of the flow chart of FIG. 5.

With reference to FIGS. 5 and 5A, the functional steps of the Process Drug Order 46 and Apply Expert Clinical Rules 50 programs of the MMU 12 and the Process Drug Order 128 program of the medical device 14 are shown in operation with the HIS 18, the caching mechanism 20 and the input device 32.

Figure 7:
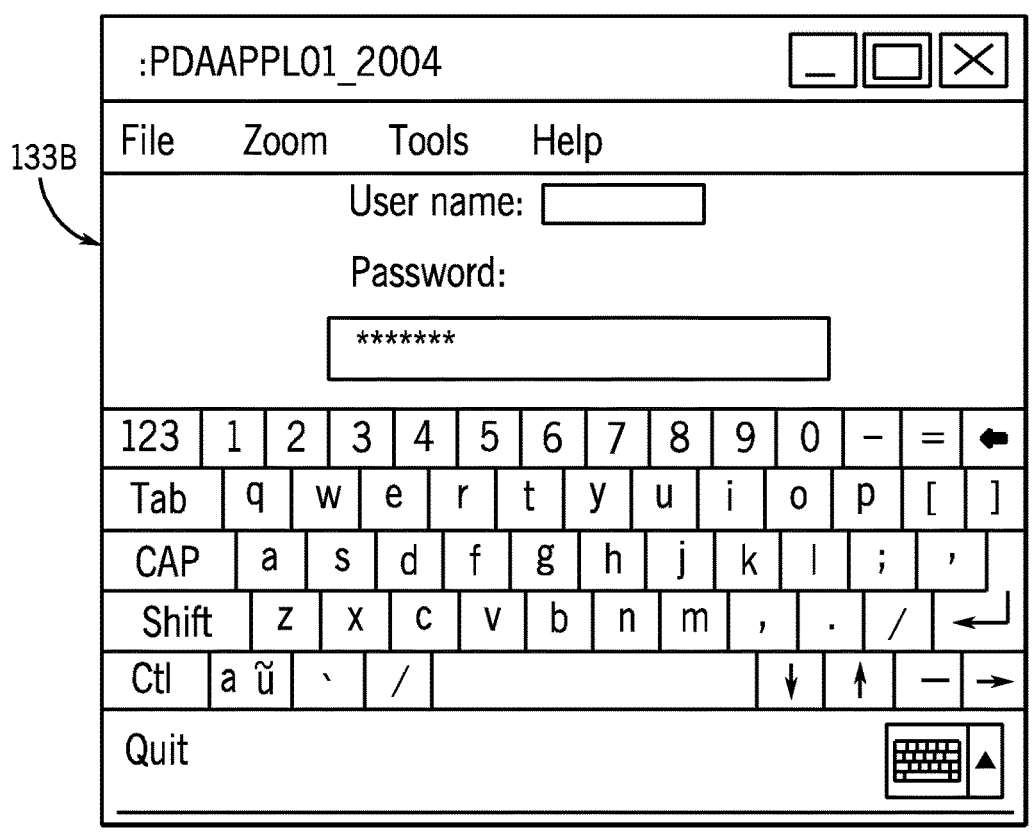
FIG. 7 is a screen shot of a delivery information input device for entry of a caregiver specific pass code.
Figure 8:
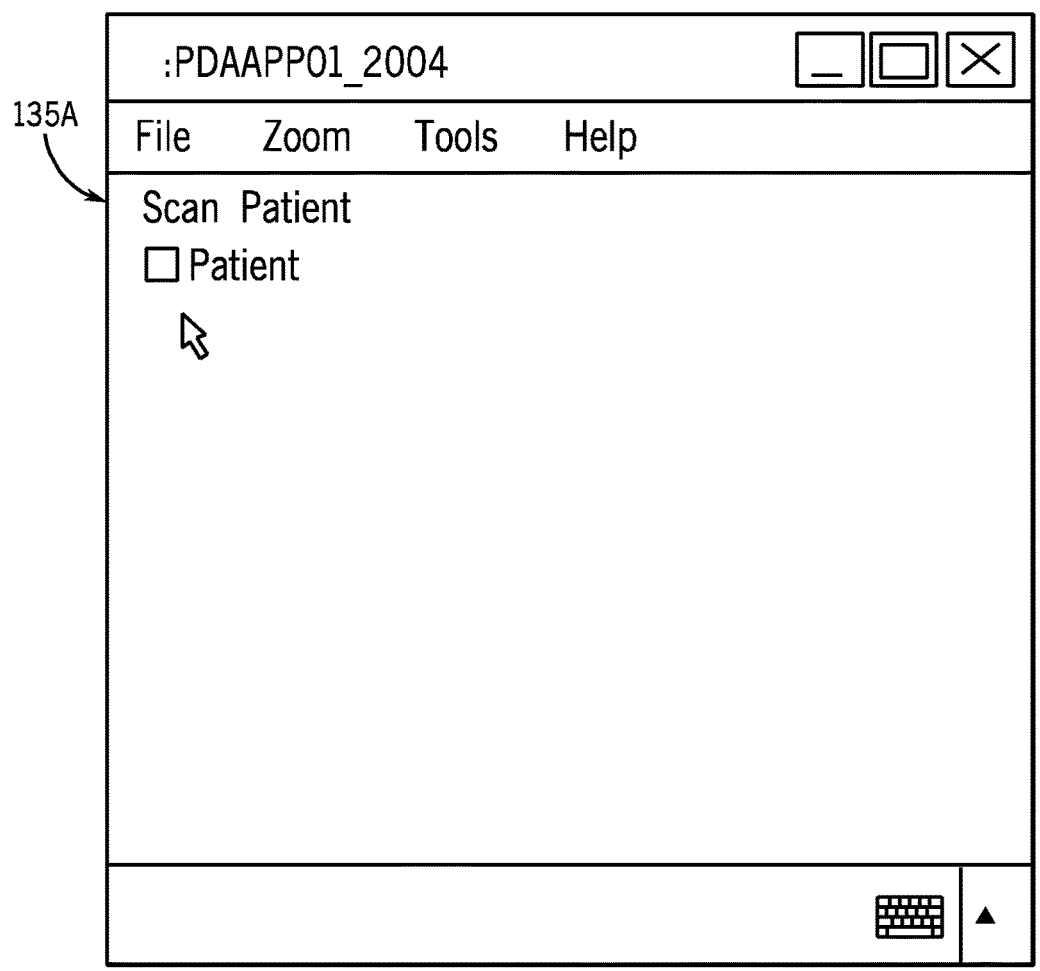
FIG. 8 is a screen shot of a delivery information input device for pulling up a scan patient option.
Figure 9:
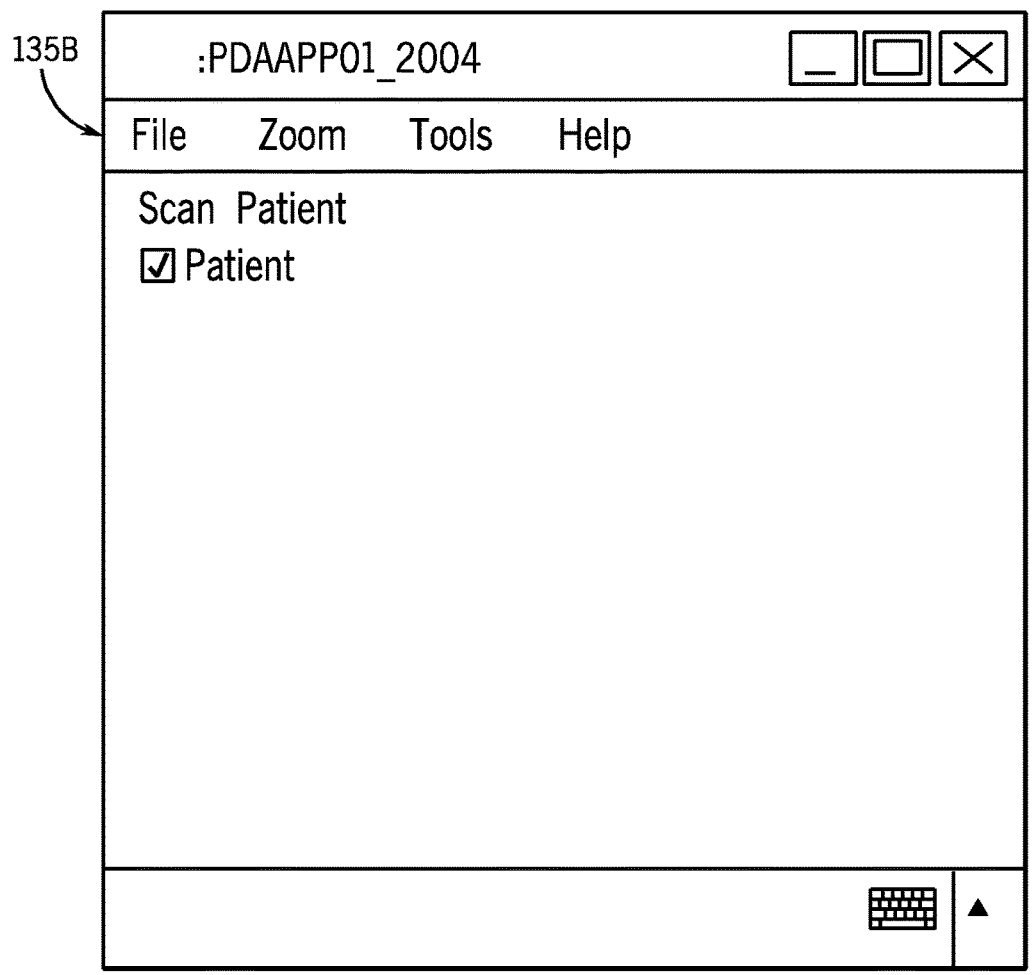
FIG. 9 is a screen shot of a delivery information input device for entry of patient-specific information.
Figure 10:
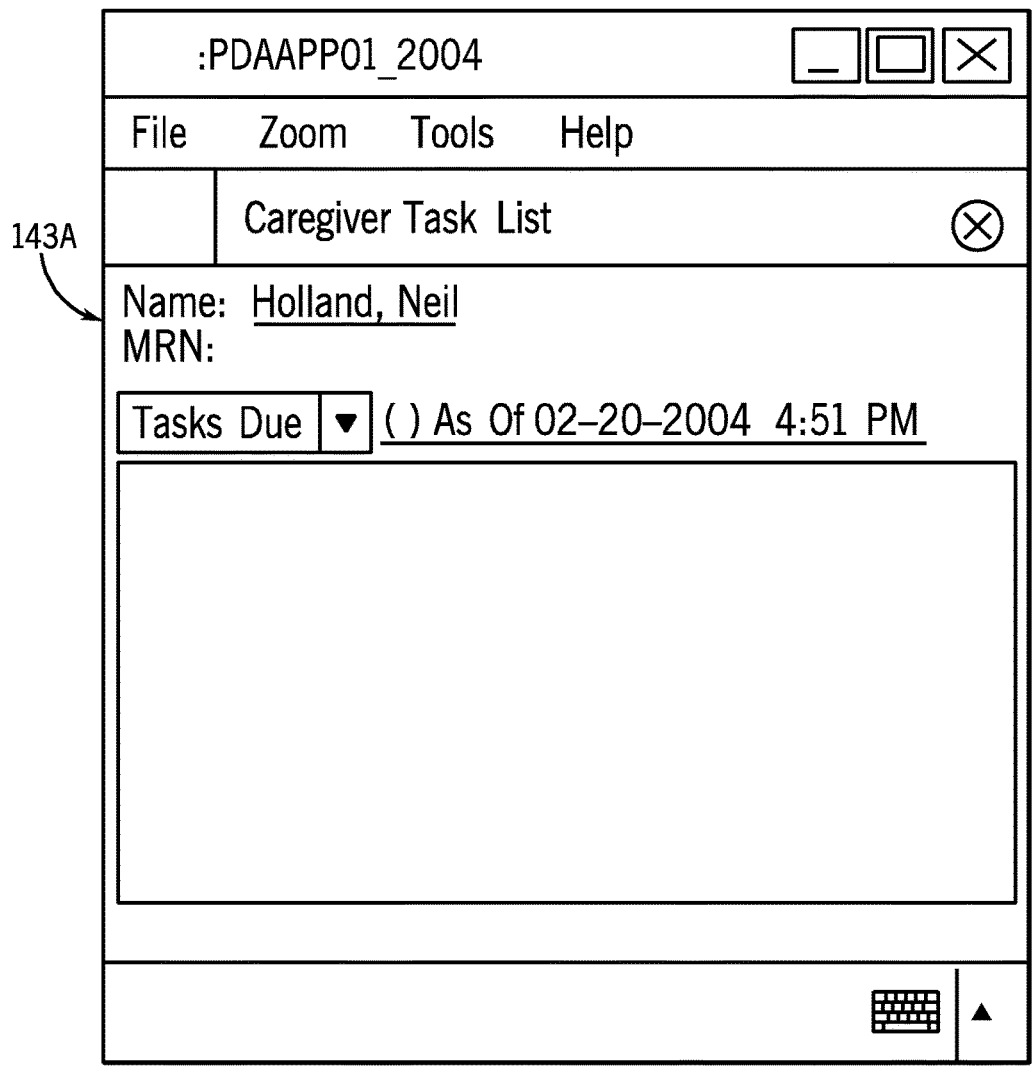
FIG. 10 is a screen shot of a delivery information input device displaying a task list.
Figure 12:
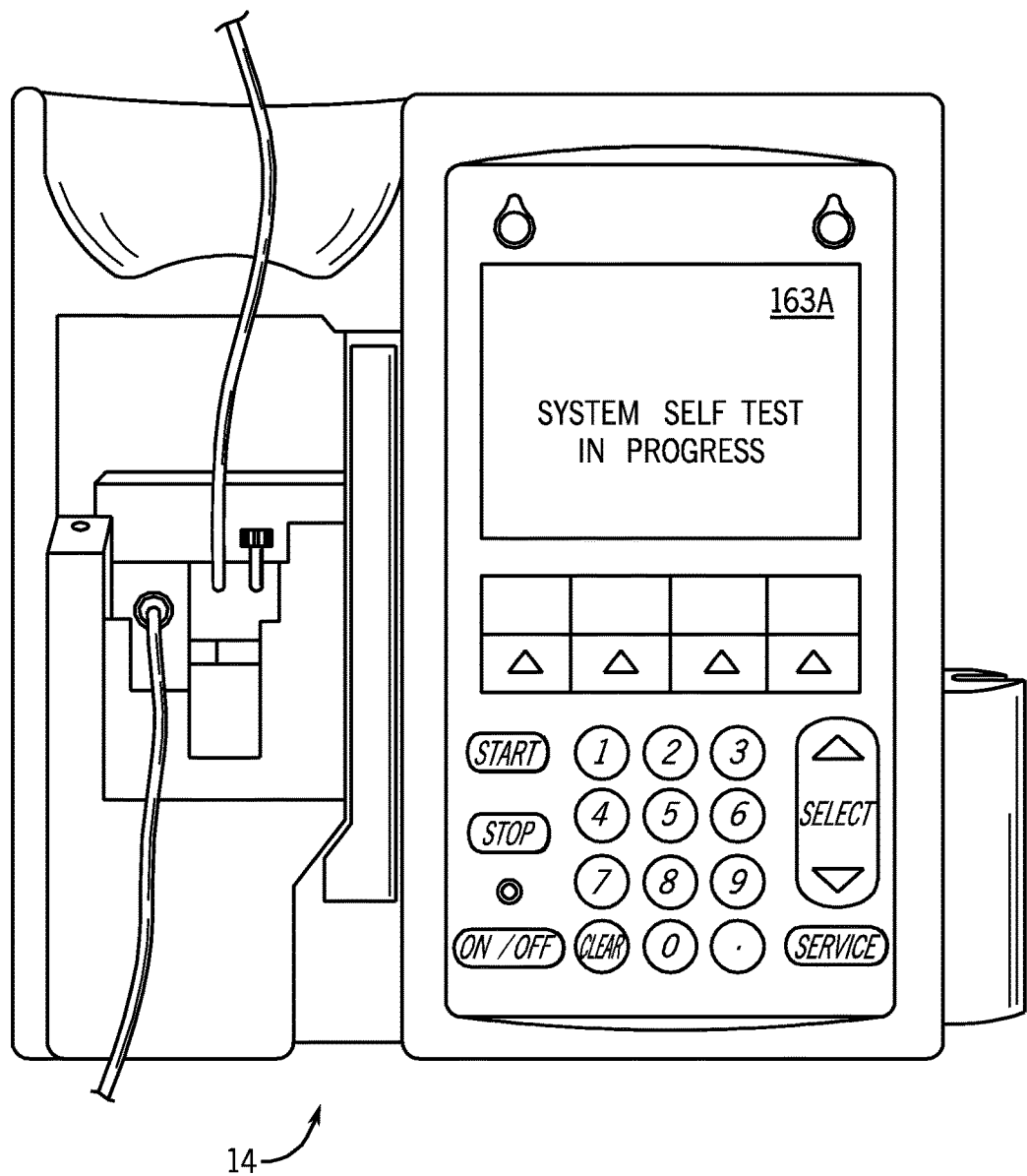
FIG. 12 is a front view of a medical device displaying a start up screen.
Figure 13:
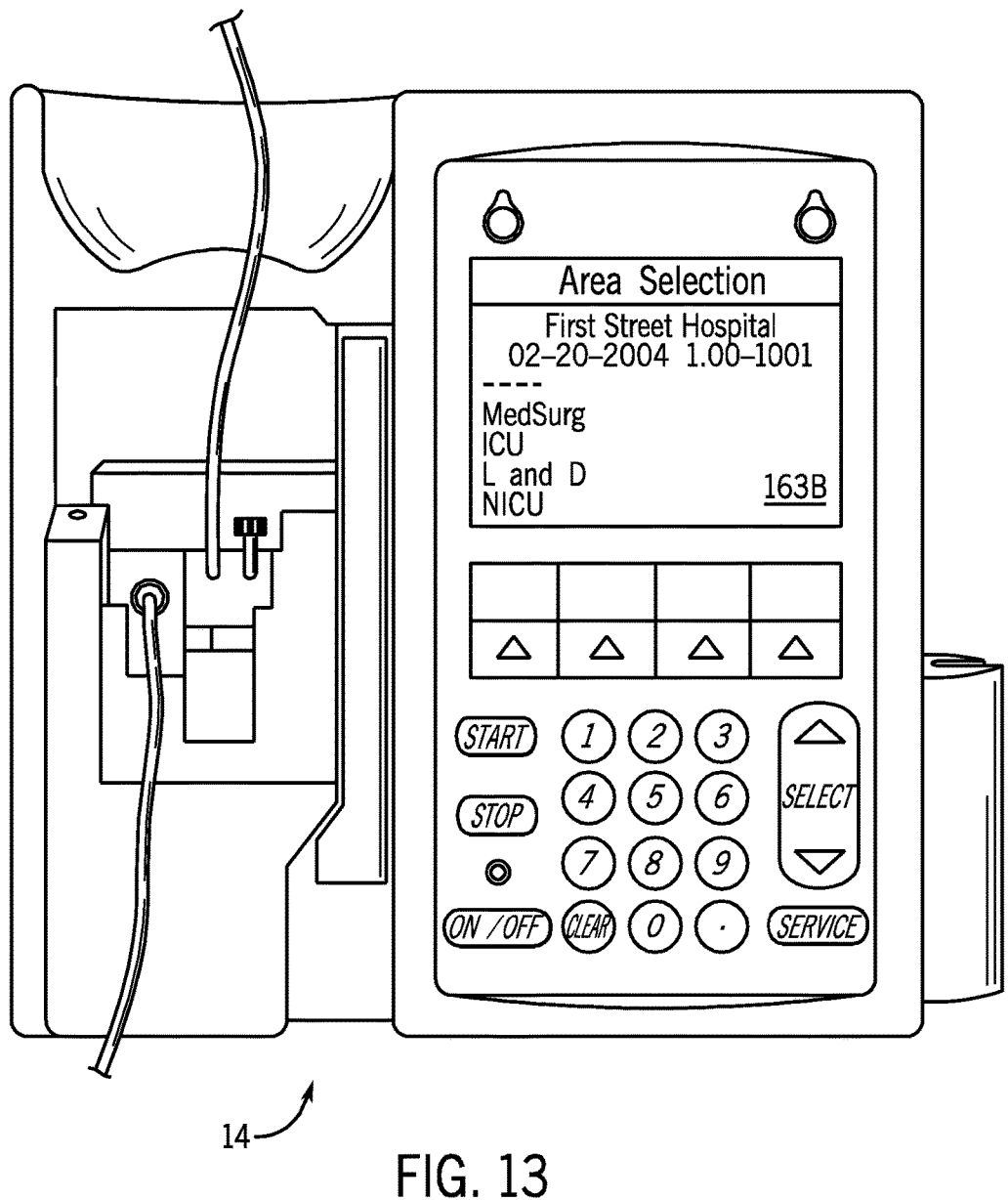
FIG. 13 is a front view of a medical device with a display and user interface means for selecting a clinical care area of a medical facility.
Figure 14:
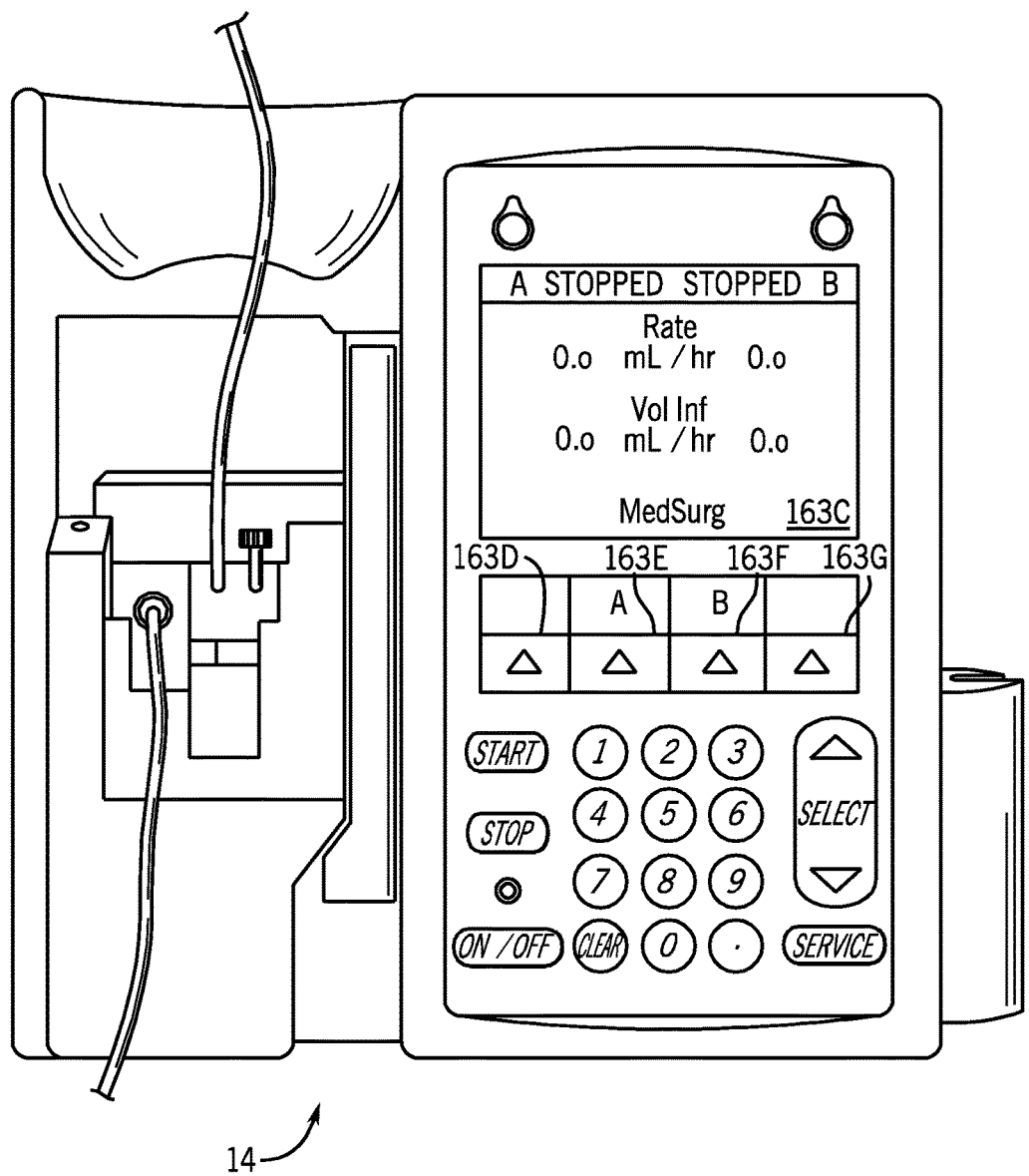
FIG. 14 is a front view of a medical device with a display and user interface means for selecting a desired input channel of the medical device.

With reference to FIGS. 4, 5 and 7, to begin to process a drug order, the input device 32 displays a default screen (not shown) on input/output device 120 which the caregiver uses to access password screen 133B (FIG. 7). The password screen 133B prompts the caregiver 114 to enter caregiver specific identification information (caregiver ID). The caregiver 114 enters caregiver ID such as a username and/or password or pass code, or the machine readable indicator 116. The input device 32 enters this caregiver ID at step 134.

With reference to FIGS. 4, 5 and 8-9, the input device 32 then displays a scan patient screen 135A (FIG. 8) which prompts the caregiver 114 to enter patient-specific identification information (patient ID). The caregiver 114 enters the patient ID such as the machine readable indicator 112. The input device 32 enters this patient ID and at step 136, and displays a confirmed scan patient screen 135B (FIG. 9) indicating that the patient ID was successfully entered into the input device 32.

With reference to FIG. 5, the input device 32 then transmits the patient ID to the caching mechanism 20 at step 138. The caching mechanism 20 transmits the patient ID to the HIS 18 at step 140. The HIS 18 retrieves a patient-specific task list and patient-specific order information based on the patient ID and transmits both to the caching mechanism 20 at step 142. The order information includes but is not limited to an order detail for a medication order, patient demographic information, and other hospital information systems data such as lab results data. The caching mechanism 20 transmits the task list to the input device 32 at step 143.

With reference to FIGS. 4, 5 and 10-11, the input device 32 then displays a task list screen 143A (FIG. 10) which prompts the caregiver 114 to accesses the task list on the input device 32. The input device 32 prompts the caregiver 114 to enter drug specific identification information (dispense ID). The caregiver 114 enters a dispense ID such as the drug container specific machine readable indicator 102. The input device 32 enters this dispense ID at step 144. The input device 32 processes the dispense ID to select the correct task from the task list, then displays a task screen 143B (FIG. 11), and transmits a dispense ID to the caching mechanism 20 requesting an order ID at step 146. The caching mechanism 20 transmits a dispense ID to the HIS 18 requesting an order ID at step 148. The HIS 18 transmits an order ID to the caching mechanism 20 at step 150. The caching mechanism 20 forwards this order ID to the input device 32 at step 152.

Alternatively, the three entered IDs (patient ID, dispense ID, and channel ID) are entered in a different specific order or without regard to order. Where the IDs are entered without regard to order, the IDs would be maintained within the MMS 10 and/or caching mechanism 20 as they are entered, so that the IDs can be recalled when needed to complete the medication delivery workflow.

The input device 32 matches the order ID with an item in the task list to ensure a Five Rights check at step 154. The "Five Rights" in this section refer to the "Five Rights of Medical Administration". Alternatively, the Five Rights check is done at the MMU 12 once the MMU 12 receives the order information as well as the patient, dispense, and channel IDs. A description of these "rights" follows. Right patient, is the drug being administered to the correct patient. Right drug, is the correct drug being administered to the patient. Right dose, is the correct dosage of the drug being administered to the patient. Right time, is the drug being administered to the patient at the correct time. Right route, is the drug being administered into the patient by the correct route, in this case intravenously through an IV. Once the order ID and item in the task list are reconciled, the input device 32 sends an order confirmed message to the caching mechanism 20 at step 156. In response, the caching mechanism 20 sends the order detail (medication order prescribed for a patient) of the order information to the input device 32 at step 158.

With reference to FIGS. 4, 5, 11, the input device 32 then displays a scan device/channel screen 143B (FIG. 11) which prompts the caregiver 114 to enter channel identification information (channel ID) regarding which channels of the medical device 14 are to be used for the delivery. The caregiver 114 enters a channel ID such as the machine readable indicator 92. The input device 32 enters this channel ID at step 160, and displays a confirmed scan device screen 159B (FIG. 11B) indicating that the channel ID was successfully entered into the input device 32. It will be appreciated that the channel ID indicator 92 can include information also identifying the medical device 14 (medical device ID). Alternatively, it is contemplated that an additional machine readable indicator (not shown) may be provided for the medical device itself separate from the channel ID machine readable indicator 92. If the medical device 14 has a single channel, a single indicator will clearly suffice. If the medical device 14 is a multi-channel device, the channel indicators can also carry information that uniquely identifies the device the channel is on. At any rate, it should be apparent that a second entry of a combined device/channel ID may be redundant and could be eliminated. The input device 32 then transmits the delivery information including caregiver ID, patient ID, medical device ID and/or channel ID, dispense ID, and order ID to the MMU 12 at step 162.

With reference to FIGS. 4, 5 and 12-14, when the medical device 14 is turned on at step 164 the medical device 14 displays a start up screen 163A (FIG. 12) on the display 88 of the medical device 14. The medical device 14 then displays a clinical care area selection screen 163B (FIG. 13) which prompts the caregiver 114 to select the clinical care area (CCA) that the medical device 14 is being assigned to. The caregiver 114 enters or selects the CCA at step 166 using scroll and select/enter keys on the user interface means 86. The medical device 14 then displays a channel selection screen 163C (FIG. 14) that prompts the caregiver 114 to select the desired channel (90 or 94) or bag source (100 or 106) using soft keys 163D-G, more particularly 163E, 163F respectively. The medical device 14 enters this channel ID at step 168. The CCA information is transmitted to the MMU 12 by the medical device 14 at step 170. Alternatively, where the CCA is known and available to the HIS 18, the CCA can be automatically generated for the medical device 14, and sent from the HIS 18 to the MMU 12

With reference to FIGS. 2 and 5, the MMU 12 executes the Process Drug Order 46 program and sends an active order request based on the delivery information from the input device 32 to the caching mechanism 20 at step 172. The caching mechanism 20 responds by sending the corresponding patient-specific order information to the MMU 12 at step 174. The caching mechanism 20 may send to the MMU 12 order information regarding all information associated with the particular patient, including but not limited to order detail for a medication order, patient demographic information, and other hospital information systems data such as lab results data or monitoring data.

Referring to FIG. 5A, the MMU 12 then executes the Apply Expert Clinical Rules 50 program to process the CCA information from the medical device 14 and the delivery information from the input device 32, at step 178. The Apply Expert Clinical Rules 50 program compares the delivery information with an expert rule set to determines expert rule set violations based on correlating treatment based protocols, disease based protocols, drug-drug incompatibility, patient data (age, height, weight, etc), vital signs, fluid in/out, blood chemistry, and status assessments (such as pain and cognition). As used herein, the term drug-drug incompatibility includes but is not limited to determinations of drug-drug interactions and/or drug-drug compatibility between two or more medication orders for concurrent delivery (to the same patient at the same time) and/or in a time sequence for the same patient (i.e. through a common output IV line). In cases where the Apply Expert Clinical Rules 50 program finds an expert rule set violation (such as a drug-drug incompatibility), the Apply Expert Clinical Rules 50 program generates an alarm and/or requires a time delay in execution for one of the two separate delivery information submissions.

The Apply Expert Clinical Rules 50 program also establishes a patient-specific rule algorithm. The patient-specific rule algorithm is primarily based on the expert rule set described above applied to a specific order detail. The patient-specific rule algorithm generates a patient-specific rule set (discussed in greater detail below, at the description of FIG. 20) according to patient-specific order information including but not limited to patient demographic information, and other hospital information systems data such as lab results data or monitoring data. The patient-specific rule set includes hard and soft dosage limits for each drug being administered. The patient-specific rule set is included in the delivery programming code sent to the medical device 14 at step 182.

Any alarms generated by the Process Drug Order 46 or Apply Expert Clinical Rules 50 programs are delivered to the medical device 14, HIS 18, and/or input device 32, computer 254 (FIG. 17), at step 180. Computer 254 can be located in a remote nurse station or a biomedical technician area. If no alarms are generated, the MMU 12 transmits a delivery program code to the medical device 14, at step 182. The delivery program code sent from MMU 12 to the medical device 14 includes a patient-specific rule set generated from any rule based adjudication at the MMU 12, including hard and soft dosage limits for each drug being administered. The medical device 14 caches the patient-specific rule set contained in the delivery program code. Alternatively, the MMU 12 can generate an alarm at the medical device 14 or another location and not download the delivery program code.

Figure 15:
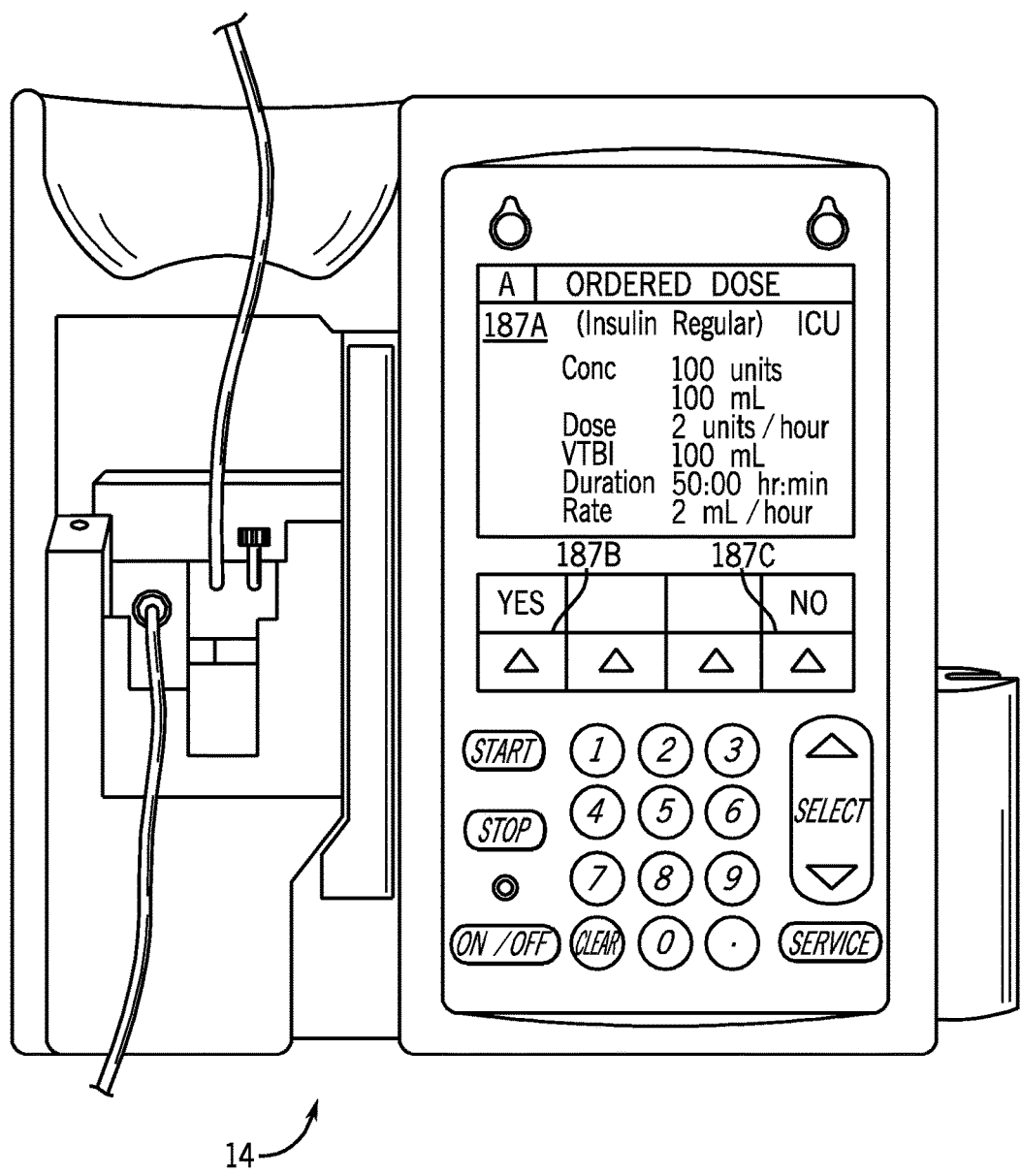
FIG. 15 is a front view of a medical device with a display and user interface means for confirming correct delivery programming code data at the medical device.

With reference to FIGS. 5, 5A and 15, the medical device 14 displays an order dose confirmation screen 187A (FIG. 15) which prompts the caregiver 114 to confirm the delivery data. As shown, the caregiver 114 selects the "yes" soft key 187B on the medical device 14 to confirm the delivery data and the "no" soft key 187C to cancel the delivery. The caregiver 114 confirms the delivery data at the medical device 14 at step 188. Once the caregiver 114 confirms the delivery data at the medical device 14, the medical device 14 then executes the delivery program code and begins infusion at step 198. As part of the program code, the infusion may be delayed for a predetermined period of time.

Alternatively, confirmation from the caregiver can be made at the input device 32 or required from both the input device 32 and medical device 14. As shown, a redundant additional confirmation performed by the caregiver 114 at the input device 32 after the medical device has received the delivery program code. Specifically, the medical device 14 transmits a canonical representation of the delivery programming code data (delivery data) to the MMU 12 detailing the infusion to be performed by the medical device 14, at step 184. The MMU 12 then transmits the same delivery data that was originally transmitted to the medical device 14 to the input device 32 at step 186. Alternatively, the delivery data can be passed to another remote computer (254 in FIG. 17), including but not limited to a computer at a nurse station, for confirmation.

With reference to FIGS. 5A and 16, the input device 32 displays an order dose confirmation screen 191A (FIG. 16) that prompts the caregiver 114 to confirm the delivery data. As shown, the caregiver 114 selects the complete button 191B on the input device 32 to confirm the delivery data and the cancel button 191C to cancel the delivery. The caregiver 114 confirms the delivery data at the input device 32 at step 192, and the confirmation is used for documentation by the HIS 18, or other systems within the hospital environment 16.

With reference to FIGS. 4A and 5A, during infusion, the medical device 14 executes its Process Drug Order 128 program. The Process Drug Order 128 program sends infusion change events and infusion time events in a delivery event log message 200 to the MMU 12. The MMU 12 forwards these delivery event log messages to the input device 32 or other system within the hospital environment 16 at step 202. The caregiver 114 acknowledges these delivery event log messages on the input device 32, at step 204. The input device 32 then sends an acknowledged delivery event log message 206 to the caching mechanism 20, detailing the delivery event, the caregiver ID, and the caregiver acknowledgment. The caching mechanism passes the delivery event message to the HIS 18 at step 208.

Once infusion has ended at step 210, the medical device 14 sends an infusion ended message 212 to the MMU 12. The MMU 12 then aggregates all the delivery event messages 200 sent during the infusion at step 214. The MMU 12 sends the aggregated delivery events 216 to the input device 32. The caregiver 114 enters a completed task 218 on the input device 32, and sends the aggregated delivery events to the caching mechanism at step 220, which in turn passes the delivery event log messages to the HIS 18 at step 222.

Figure 6:
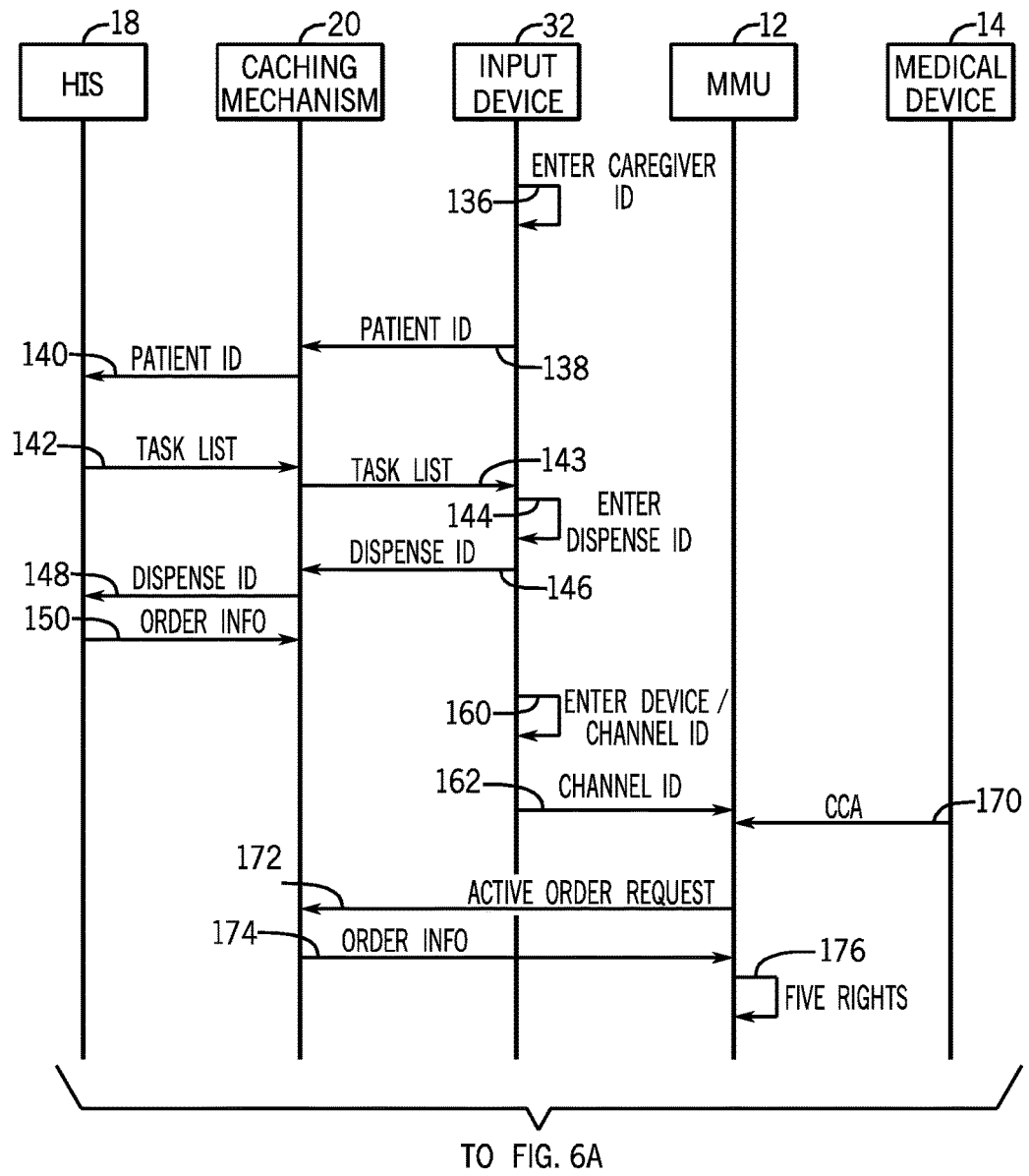
FIG. 6, is an alternative flow chart of the medication management system processing a drug order through the medication management unit and medical device, and integrated with an information system according to the invention.
Figure 6A:
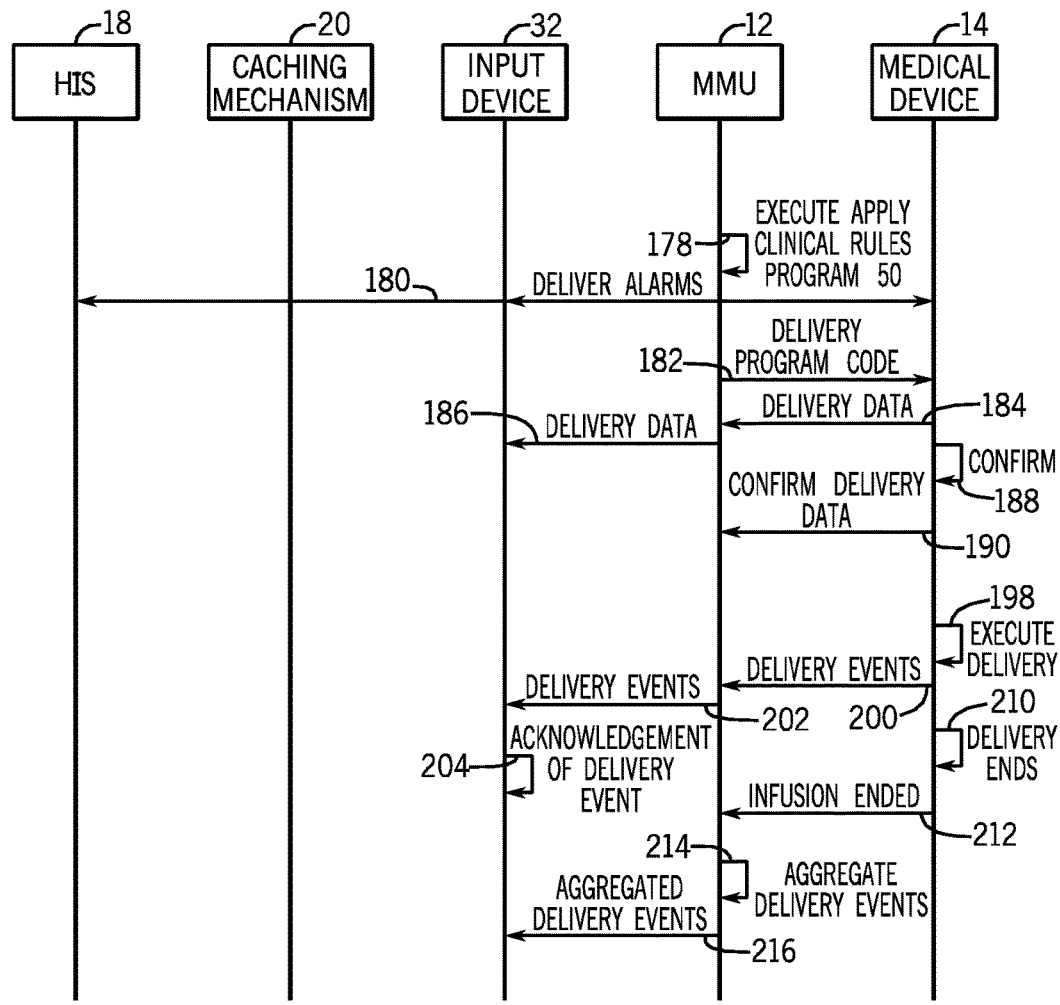
FIG. 6A is a continuation of the flow chart of FIG. 6.

With reference to FIGS. 6 and 6A, an alternative flow chart of the MMS 10 processing a drug order through the MMU 12 and medical device 14 is shown. With reference to FIGS. 4, 6 and 6A, the caregiver 114 enters the patient ID, which then is stored in the caching mechanism 20. The caching mechanism 20 transmits the patient ID to the HIS 18 and retrieves a patient-specific task list for that patient ID. The caregiver 114 then enters the dispense ID, which subsequently is stored in the caching mechanism 20. The caching mechanism 20 transmits the dispense ID to the HIS 18, and retrieves a patient-specific order information, including but not limited to an order detail, patient demographic information, and other hospital information systems data such as lab results data. The caregiver 114 then enters the channel ID, which is stored in the MMU 12.

Alternatively, the three entered IDs (patient ID, dispense ID, and channel ID) are entered in a different specific order or without regard to order. Where the IDs are entered without regard to order, the IDs would be maintained within the MMS 10 and or caching mechanism 20 as they are entered, so that the IDs can be recalled when needed to complete the medication delivery workflow.

Upon receipt of the channel ID, the MMU 12 requests the order information (order detail, patient demographic information, and other hospital information systems data) and retrieves it from the caching mechanism 20. This order information is stored within the MMU 12 and utilized for subsequent rule processing such as "Five Rights" checking and other rule set algorithms. The Process Drug Order 46 program processes the delivery information from the input device 32 (including caregiver ID, patient ID, medical device/channel ID, and dispense ID) and compares this delivery information with the corresponding order detail portion of the order information from the caching mechanism 20, at step 176. Where the order information and delivery information do not match, the device program code downloaded to the medical device 14 at step 182 includes an alarm message indicating that the five rights check was not met. Additionally, the alarm message can include a description of which particular right(s) did not match. Alternatively, the NMU 12 can generate an alarm at the medical device 14 or another location and not download the program code for delivery of the medication order.

Alternatively, the MMU 12 can accept a Five Rights check from another device, such as a HIS 18 or an input device 32. This check can be accepted either by a direct data element being sent to the MMU 12 indicating a Five Rights check, or implied through the workflow provided by the HIS 18 or input device 32.

The other steps shown in FIGS. 6 and 6A are similar to corresponding steps in FIGS. 5 and 5A. Accordingly, these steps will not be described with any further detail here. One skilled in the art will appreciate that the vertical lines in FIGS. 5, 5A, 6, 6A do not necessarily represent a firm time sequence. Some steps may be done sooner than shown (for example, turning on the medical device) or later than shown (for example, aggregate delivery events).

With reference to FIGS. 2, 4A, 5, 5A and 20, in one embodiment, the Process Drug Order 46 program of the MMU 12 and the corresponding Process Drug Order 128 program of the medical device 14 permit the MMU 12 to remotely control the medical device 14 to modulate performance of a medication order. For example, the MMU 12 can remotely start and/or stop the medical device 14. Once the delivery program code is received by the medical device 14 at step 184, the Process Drug Order 46 of MMU 12 remotely starts execution of the infusion by sending a start order 224, which triggers the medical device to begin infusion at step 225. Likewise, when the infusion is to end at step 228, the Process Drug Order 46 program can remotely stop the infusion by sending a stop order 226 to the medical device 14, which triggers the medical device to end infusion at step 228. In most cases, the MMU 12 requires the caregiver to confirm the start or stop of execution. This confirmation by the caregiver may take place at the input device 32 or the medical device 14. However, one skilled in the art will appreciate that there may be emergency situations where an order could and should be stopped without human confirmation.

With reference to FIGS. 2, 5, 5A and 20, in one embodiment, the Apply Expert Clinical Rules 50 program of the MMU 12 permits the MMU 12 to adjust a previously fixed patient-specific rule set based on new patient conditions and/or recent lab results, and notify the caregiver that adjustment is recommended by the MMU 12. As discussed above in regard to FIGS. 5 and 5A, the Apply Expert Clinical Rules 50 program establishes a patient-specific rule algorithm. The patient-specific rule algorithm is primarily based on the expert rule set described above applied to a specific order detail. The patient-specific rule algorithm generates a patient-specific rule set according to patient-specific order information including but not limited to patient demographic information, and other hospital information systems data such as lab results data or monitoring data. The patient-specific rule set includes hard and soft dosage limits for each drug being administered, and these hard and soft dosage limits likewise are adjusted when the patient-specific rule set is adjusted.

Figure 20:
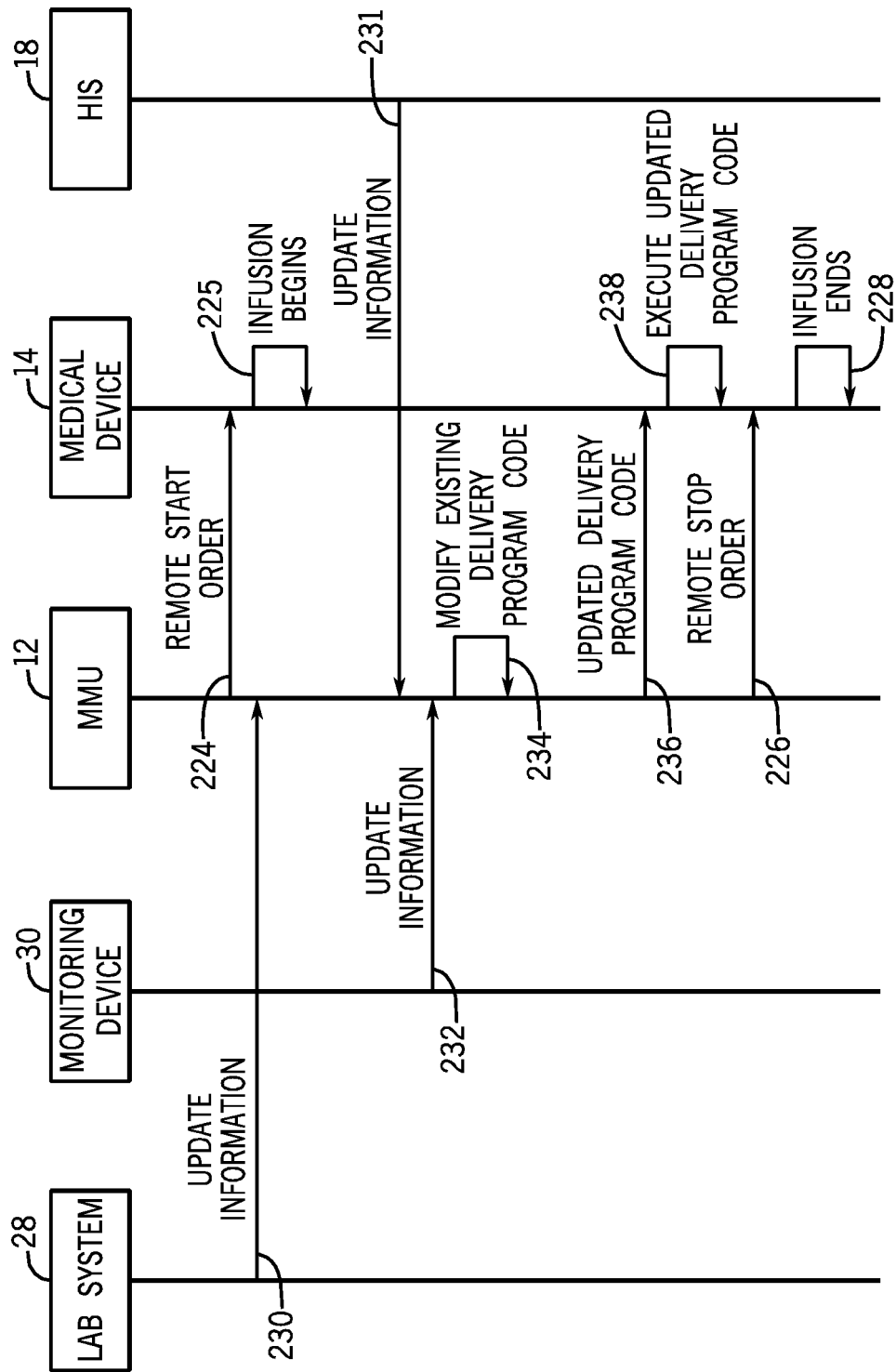
FIG. 20 is a flow chart of the medication management system updating a delivery program code executed on the medical device based on new information from a lab system, HIS and/or monitoring device.

For example, during or even before an infusion, the MMU 12 may receive updated patient information that can impact an ongoing or impending infusion. As shown in FIG. 20, the lab 28 sends updated patient-specific lab results to the MMU 12 at step 230. Likewise, the monitoring device 30 sends updated patient-specific monitoring information to the MMU 12 at step 232. Additionally the MMU 12 queries the HIS 18 for patient information including: Patient Allergies, Patient Diet, and Current Patient Medical Orders. Patient Allergies are used to check for drug-allergy interactions, at step 231. Patient Diet information is used to check for drug-food interactions. Current Patient Medical Orders are used to check for drug-drug incompatibility. Like the patient information gathered from the Lab 28 and the monitoring device 30, the patient information from HIS 18 is also used by the MMU 12 to update the delivery program order.

As shown in FIGS. 5 and 5A, in cases where the MMU 12 is processing a drug order for the medical device 14, the MMU 12 executes the Apply Expert Clinical Rules 50 program at step 178 to establish a patient-specific rule set based on updated patient information received or retrieved from the lab 28, the monitoring device 30, and or the HIS 18 (FIG. 20). This real-time or near delivery time updated patient-specific information is useful in adapting patient therapy because it may not have been available at the time the medication order was prescribed.

As shown in FIG. 20, The MMU 12 also modifies the existing patient-specific rule set in the existing delivery program code at step 234 based on updated patient information received or retrieved from the lab 28, the monitoring device 30, and or the HIS 18. The MMU 12 optionally alerts the input device 32 and/or the medical device 14 of changes to the patient-specific rule set. MMU 12 also optionally generates an alert message if the delivery programming code violates any parameter of the adjusted hard and soft dosage limits. Additionally, the MMU 12 optionally requests confirmation by the caregiver prior to instituting the new patient-specific rule set. The MMU 12 then delivers an updated delivery program code to the medical device 14 for execution at step 236. The medical device 14 then executes this updated delivery program code as step 238. The updated delivery program code sent from MMU 12 to the medical device 14 includes an updated patient-specific rule set generated from any rule based adjudication at the MMU 12, including hard and soft dosage limits for each drug being administered. The medical device 14 caches the updated patient-specific rule set contained in the delivery program code. Additionally, the MMU 12 collects, stores, and reports the changes to the patient-specific rule set, changes to the hard and soft limits, as well as the history of each medication order.

An example of how the MMU 12 updates the patient-specific rule set based on lab results or monitored patient conditions is provided below with respect to the drug Heparin, which is a blood thinner. The medication order entered by the physician might be:

Give heparin 1000 units/hour. If the activated partial thromboplastin time (APTT)>75 seconds then decrease heparin to 800 units/hour.

If the medical device 14 has started the infusion at 1000 units/hour and the MMU 12 subsequently receives an updated APTT value of 100 seconds from the lab 28 on the patient, the MMU automatically commands the medical device 14 to decrease the infusion rate to 800 units/hour. Alternatively, when the MMU is notified by lab 28, an alarm will be generated to the PDA 32 and/or the medical device 14 to notify the caregiver of the need to change the infusion rate. The MMU can preprogram the pump for the caregiver to confirm the recommended change.

In further embodiment or method, the hospital may establish expert rules or clinical decision support rules in the MMU 12 that will be applied automatically to incoming prescribed orders, such that the physician may simply write an order for 1000 or 1200 units/hour. The hospital best practices formulated by the appropriate medical personnel are established in the MMU 12 and can dictate that all heparin orders are to be conditioned on the APTT lab result and such an expert rule or clinical decision support rule will be used by the MMU 12 to govern the operation of the medical device 14. The MMU 12 also can check the most recent patient data and provide an alarm and/or temporarily modify the delivery order prior to the start of the infusion if the prescribed order is no longer appropriate given the expert rules or clinical decision support rules and the latest lab results or monitored patient conditions. It should be apparent that this kind of intervention by the MMU 12 during or immediately prior to an infusion is particularly useful in preventing adverse consequences for the patient and the hospital.

Where the MMU 12 adjusts a previously fixed patient-specific rule set based on new patient conditions and/or recent lab results, as described above, the MMU 12 provides dynamic advanced reports of real-time rule set changes in relation to changes in the condition of the patient (an "information cascade"). These advanced reports detail the history of both hard and soft upper and lower limits, as well as the activation of overrides and confirmations based on these limits for each medical device 14 managed by the MMU 12. Further details on this feature can be found in commonly owned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

Figure 19:
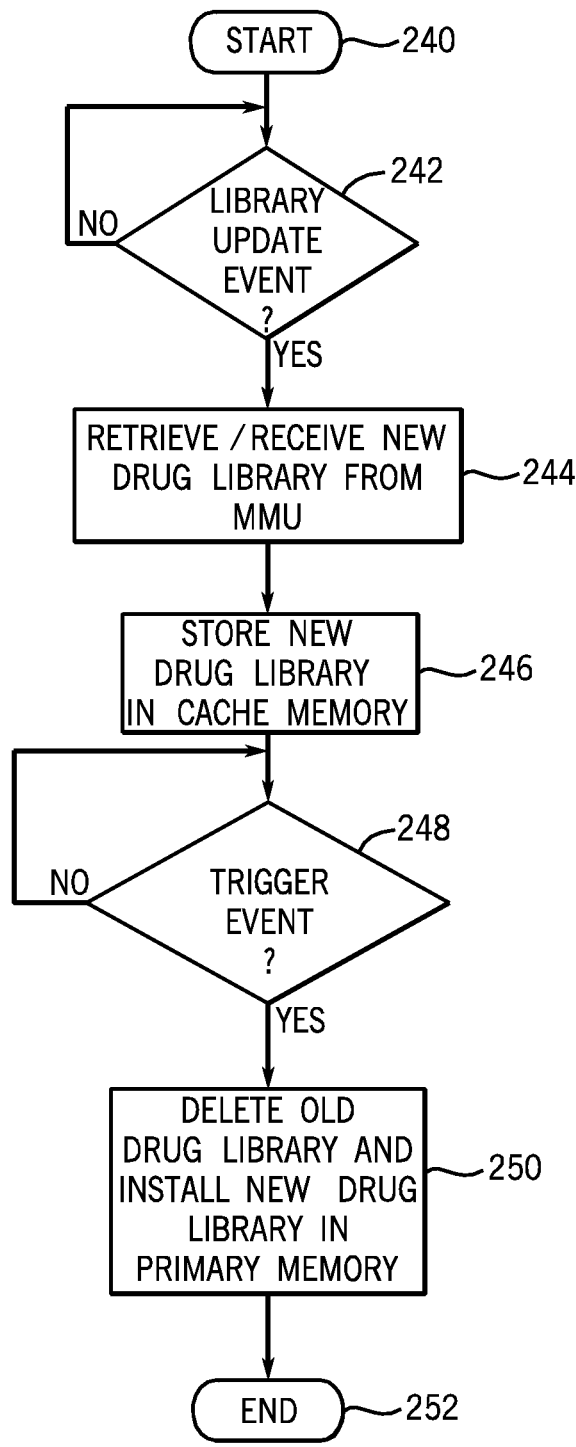
FIG. 19 is a flow chart of the medical device retrieving/receiving an updated drug library from the medication management unit.

With reference to FIGS. 2, 4A and 19, the Download Drug Library 44 program in the MMU 12 and the corresponding Download Drug Library 132 program in the medical device 14 operate to send a drug library to the medical device 14 from the MMU 12. The drug library includes drug and device related information, which may include but is not limited to drug name, drug class, drug concentration, drug amount, drug units, diluent amount, diluent units, dosing units, delivery dose or rate, medication parameters or limits, device/infuser settings and/or modes, CCA designations and constraints, and library version. The Download Drug Library 132 program is designed to cache in a cache memory 126A a new database or drug library at medical device 14 while maintaining an existing older version database or drug library in its primary memory 126. This allows the medical device to operate or deliver an infusion based on the older version of the drug library without disruption until a trigger event occurs, at which time the new drug library replaces the older version in the primary memory 126. It is contemplated that the medical device 14 can be equipped with an initial drug library at the factory.

The Download Drug Library 132 program in the medical device 14 begins at a block 240 and at block 242 a determination is made that a drug library update needed event has occurred. For instance the drug library update needed event could be a completed infusion, a stopped infusion, elapsed time, a specific date and time, creation of the new drug library, the medical device 14 being or entering into a particular configurable mode such as stop, "sleep" or "wakeup", connection of the medical device 14 to an access node 84 in a new CCA, a download of a new or modified drug library to the medication management unit, or a determination that the existing drug library at the medical device needs updating. The configurable mode could be any number of device modes including a power-on sleeping mode and a power-off mode. The determination that a drug library update needed event has occurred can be made by (at) the MMU 12, the medical device 14 or by a combination of the two.

Based on the specific drug library update needed event, the Download Drug Library 132 proceeds to block 244 where it retrieves or receives a new drug library. Once retrieved or received, the Download Drug Library 132 proceeds to block 246 where it stores the new drug library in the cache memory 126A of the medical device 14. While a medical device 14 is operating on a patient or in an otherwise nonconfigurable mode, information such as a new drug library or database is stored in a cache memory 126A of the medical device 14 as the information is received from a wired or wireless link through the network interface 122. The Download Drug Library 132 proceeds to block 248 where it determines if a specific trigger event has occurred. For instance, the trigger event could be a completed infusion, a stopped infusion, a determination that the device is in a configurable mode, elapsed time, a specific date and time, creation of the new drug library, a download of a new or modified drug library to the medication management unit, and a determination that the existing drug library at the medical device needs updating. The configurable mode could be any number of device modes including a power-on sleeping mode and a power-off mode. The determination that a trigger event has occurred can be made by (at) the MMU 12, the medical device 14 or by a combination of the two.

The Download Drug Library 132 then proceeds to block 250 where it deletes the existing drug library in primary memory 126 and installs the new drug library, and the new drug library from cache memory 126A will replace the older information in the memory 126 of the medical device 14. The Download Drug Library 132 process is then complete and ends in block 252.

Additional related features of the Download Drug Library 44 program in the MMU 12 and the corresponding Download Drug Library 132 program include recording the history of the download, verify the correct download, notification to the caregiver of a change of library, and a preliminary note on the medical device 14 display stating that the drug library will be changed after any current infusion (i.e., before the next infusion).

Additionally, partial updates of the drug database within the medical device 14 are also made possible by the present invention. The MMU 12 is supplied with a drug database that allows a user to update a single data item (row, column, or cell) in the database without re-writing the entire database. This provides faster processing and downloading times when modifying the drug database.

Further, the Download Drug Library 44 program in the MMU 12 is designed to modify a medication library from the HIS 18 in such a way that only a single configuration of a single drug library is necessary to provide download information to multiple separate and different medical devices 14 where each device has unique parameters (different models, processors, computer architecture, software, binary format, or manufacturers, for example). In this embodiment, the configured drug library is designed so that only a subset of the configured drug library is specific for each unique type of medical device 14, and only the specific information is selected for transfer to each medical device 14. Additionally, pre-validation of the configured drug library is done through use of a rule set editor prior to sending from the MMU 12 to the medical device 14, and post-validation occurs where the medical device 14 confirms receipt of an acceptable drug library back to the MMU 12. Further details on these additional related features can be found in commonly owned co-pending application entitled SYSTEM FOR MAINTAINING DRUG INFORMATION AND COMMUNICATING WITH MEDICATION DELIVERY DEVICES filed on Feb. 20, 2004, which is expressly incorporated herein in its entirety.

With reference to FIGS. 2, 3, and 4A, the Monitor Pump 44 program in the MMU 12 and the corresponding Monitor Pump 130 program in the medical device 14 operate to map the approximate or general physical location of each medical device 14 within the hospital environment and to enable a user to trigger a locator alarm to locate a particular medical device 14. Additionally, the programming enabling the medical device locator would be located in an asset manager 64 portion of the MMU 12.

Figure 17:
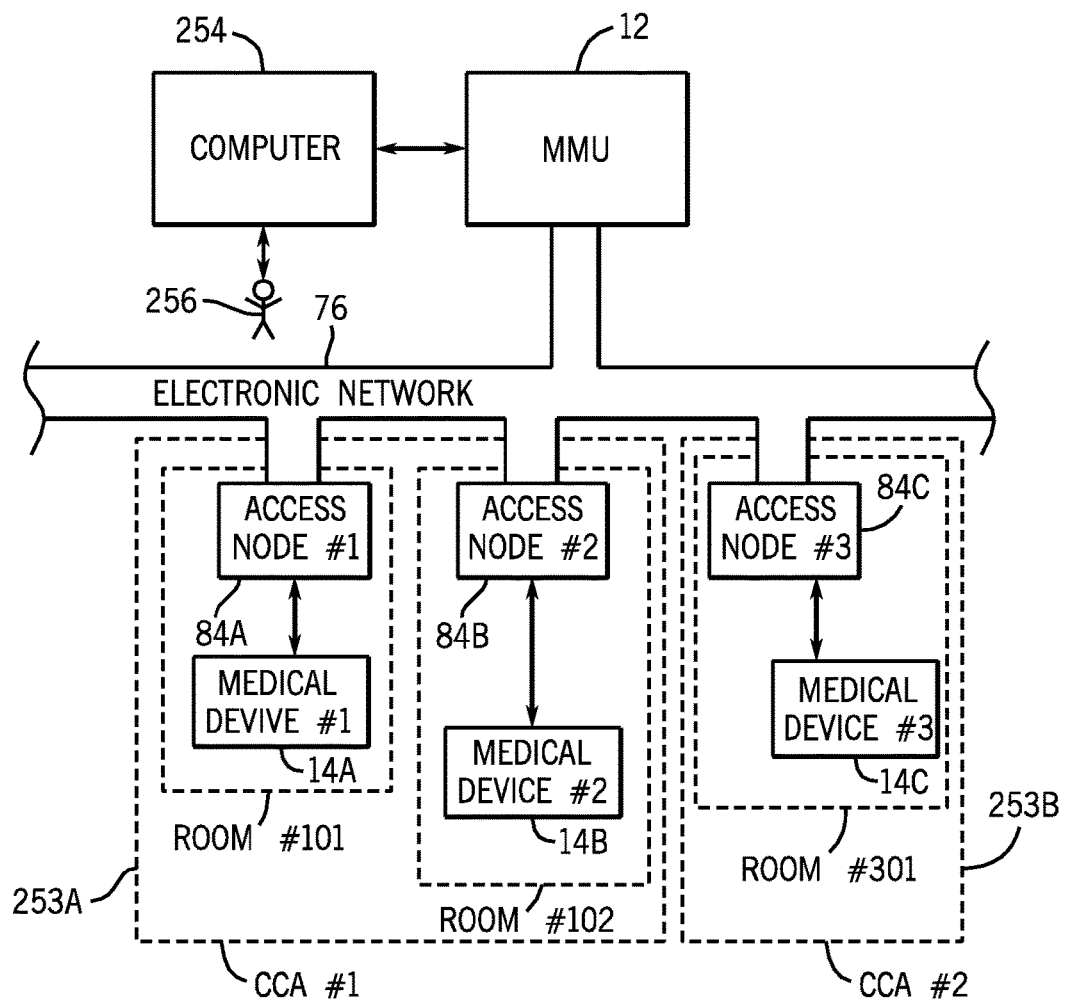
FIG. 17 is a schematic diagram of the medication management system including a medication management unit and one or more medical devices, showing the medication management unit communicates with a medical device to locate the device.

With reference to FIG. 17, the MMU 12 communicates with one or more (more preferably a plurality of) medical devices 14A, 14B, and 14C through the electronic network 76. The medical device or devices 14A, 14B, and 14C connect to the electronic network 76 through one or more (more preferably a plurality of) access nodes 84A, 84B, and 84C distributed in one or more (more preferably a plurality of) CCAs 253A and 253B. More than one medical device 14 can operate from an individual access node 84 and be associated with a particular patient. Typically, there is one access node per room (101, 103, and 301), but it also is possible to have more than one access node per room and more than one room or CCA per access node. Additionally, as discussed above with regard to FIG. 4, the connection between the medical devices 14A, 14B, and 14C and the access nodes 84A, 84B, and 84C can be wireless. A user access device such as a computer system 254 is remotely located from the MMU 12 and the medical device 14 and communicates with the MMU 12 to permit a user 256 to activate the Monitor Pump 44 program in the MMU 12 and remotely activate the corresponding Monitor Pump 130 program in the medical device 14. The computer 254 can be located in a variety of locations, including but not limited to a nurse station or a biomedical technician area.

Figure 18:
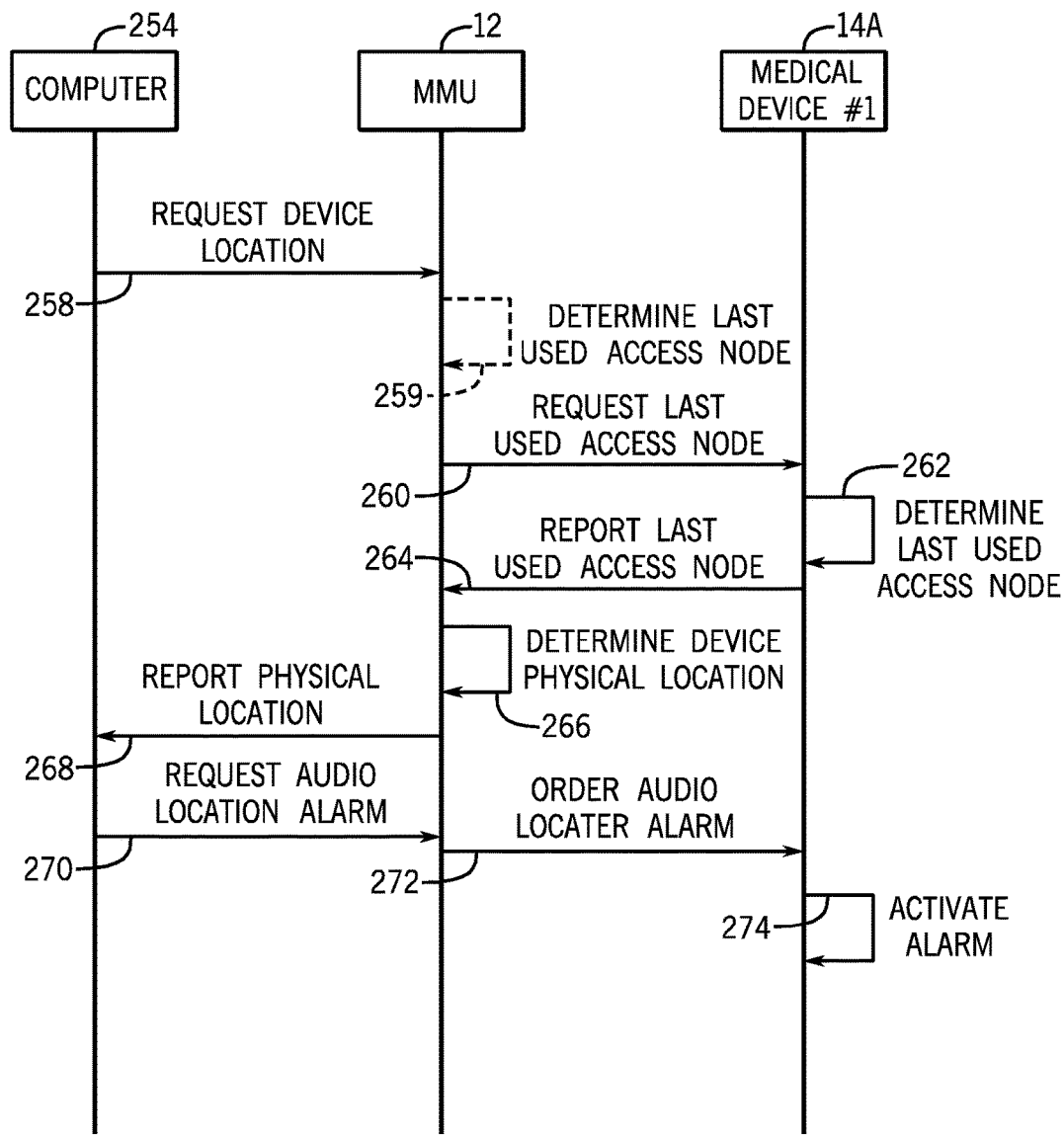
FIG. 18 is a flow chart of the medication management system locating a medical device.

With reference to FIG. 18, the functional steps of the Monitor Pump 52 program in the MMU 12 and the corresponding Monitor Pump 130 program in the medical device 14A are shown in operation with the computer 254. To begin to request a physical location for a medical device 14, the user 256 (not shown) enters a query for the location of a medical device 14A. The computer 254 sends a request device location 258 message to the MMU 12. The MMU 12 in turn sends a request last used access node 260 message to the medical device 14A. It is also contemplated that the Monitor Pump Program 130 can be operated with the input device 32.

The medical device 14A determines the last access node 84A-84C used to connect with the electronic network 76 at step 262. A report of the last used access node 264 is sent from the medical device 14 to the MMU 12. The MMU 12 processes the report of the last used access node 264 to determine the general physical location of the device at step 266. Once the physical location of the medical device 14A is determined by the MMU 12, a report physical location 268 message is sent from the MMU 12 to the computer 254. Additionally, the MMU 12 tracks "change of infuser access node" events, when a medical device 14 begins to communicate through a different network access node 84. The MMU 12 communicates the physical locations of medical devices 14 to the HIS 18.

If the user 256 requires additional assistance in locating the particular medical device 14A, the user 256 can instruct the computer 254 to send a request audio location alarm 270 message to the MMU 12. The MMU 12 in turn sends an order audio locator alarm 272 message to the medical device 14A. The medical device 14A then activates an audio alarm at step 274 to assist the user 256 in locating the medical device 14A. The audio alarm activation can be delayed by a predetermined time to allow the user time to travel to the area of the last used access node. The audio alarm feature is useful in allowing the user to more precisely pinpoint the location of the medical device 14. The audio alarm feature is particularly useful if the medical device 14 is very close to other medical devices or has been moved to a storage closet or other location where it is not readily apparent visually.

Alternatively, the functional steps of the Monitor Pump 44 program in the MMU 12 and the corresponding the Monitor Pump 130 program shown in FIG. 18 can be performed as a series of "push" steps instead of a series of "pull" steps (as shown in FIG. 18). In a "push" embodiment the medical device 14A periodically determines the last used access node and periodically reports the last used access node to the MMU 12 as a "here I am" signal. Likewise, the MMU 12 periodically determines the physical location of the medical device 14A based on the last access node 84A used by the medical device 14, and periodically reports the physical location of the medical device 14A to the user access device 254. Alternatively, the MMU 12 programming allows it to determine which of access nodes 84 was the last access node used by the device 14 (step 259 indicated by a dashed line) and the MMU can report the general physical location of the medical device 14 to the computer 254 without requesting a report from the medical device 14.

Figure 21:
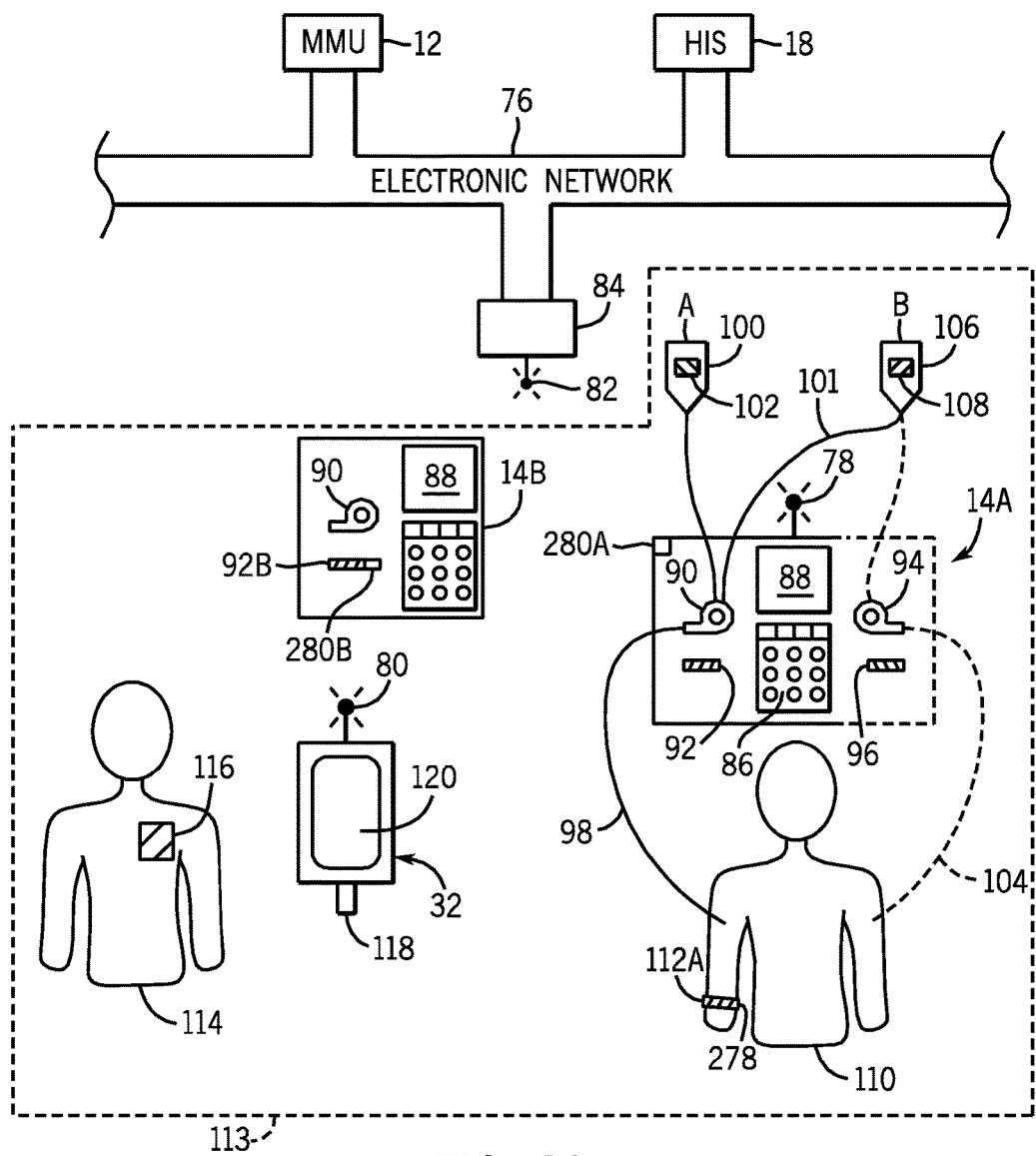
FIG. 21 is an alternative pictorial schematic diagram of the medication management system and its interaction with medical devices and the information system.

In one embodiment described above, the association between medical devices 14, patient 110, drug 100, and caregiver 114 (if present), is accomplished by swiping machine readable indicators on each of these elements of the PAN 113 (See FIG. 4). This association is made in software residing the MMU 12. Alternatively, the association is made in software residing in the medical device 14. With reference to FIG. 21, in another embodiment, the association between medical devices 14A, patient 110, drug 100, and caregiver 114, is accomplished by "auto-association". Auto-association is desirable in situations where the patient's wrist is not readily accessible (e.g. during surgery, or a neonate in an incubator).

In the auto-association embodiment, the MMU 12 and medical device 14A are designed to establish the patient as the focus of the MMS 10. In this embodiment, the patient 110 is equipped with a machine readable indicator 112A on a wristband, toe tag, badge or similar article. The machine readable indicator 112A contains transmitter/receiver chip 278, capable of short-range transmission. The transmitter/receiver chip 278 is a low power RF Bluetooth™, a dedicated RF transmitter working with a PIC processor, or any other suitable transmitter/receiver. The patient 110 is fitted with the machine readable indicator 112A at the time of admission. The unique ID number of the particular machine readable indicator 112A is stored with an electronic patient record at the HIS 18 and hence MMU 12. The MMU 12 is thereby notified of the particular machine readable indicator 112A associated with the particular patient 110. Additionally, it is contemplated, that any other machine readable indicator used with the present invention, may also contains transmitter/receiver chip capable of short-range transmission. For instance, the caregiver machine readable indicator 116 and medication machine readable indicator 102 may also be equipped with a transmitter/receiver chip.

Each medical device 14A is also equipped with a transmitter/receiver chip 280A. Upon placing a medical device 14 at the patient 110 bedside, within the PAN 113, the transmitter/receiver chip 280A of the medical device 14A "pings" by sending out a "request for patient" command to any transmitter/receiver chip 278 that is in the area. Each transmitter/receiver chip 278, which is in the area (usually about 0-10 meters, more preferably about 0-3 meters), replies to the ping by sending the transmitter/receiver chip 280 of the medical device 14A the unique ID number of the particular machine readable indicator 112A. Upon receipt of a signal from the machine readable indicator 112A, the medical device 14A places the ID number of the machine readable indicator 112A in memory 126 (See FIG. 4A) and also transmits the same to the MMU 12. Alternatively, the unique ID of the indicator 112A can be transmitted directly to an MMU 12 located in the area or indirectly through another route, including but not limited to the medical device 14. With reference to FIGS. 5, 5A, 6 and 6A, the MMU 12 Process Drug Order 46 program then checks the patient ID entered at step 162 and the device/channel ID entered at step 160 to ensure the correct match. The MMU 12 associates the medical device 14A only to the identified patient based on the patient ID number sent to the MMU 12. Dissociating the medical device 14A from the patient is done based on a command from a user, or other method.

It should be noted, that the machine readable indicator 112A (as well as the machine readable indicator 112), can include equipment for monitoring the wearer, and transmitting this monitored information to the medical device 14 and/or the MMU 12.

With reference back to FIG. 21, placing a second medical device 14B within the PAN 113 leads to a repeat of the same process. In this case the first medical device 14A "pings" any transmitter/receiver chip that is in the area. The transmitter/receiver chip 280B of the second medical device 14B replies to the ping by sending the transmitter/receiver chip 280A of the first medical device 14A the unique ID number of the particular machine readable indicator 92B. Upon receipt of a signal from the machine readable indicator 92B, the first medical device 14A places the ID number of the machine readable indicator 92B in memory 126 (See FIG. 4A) and also transmits the same to the MMU 12. The patient ID number is then sent from the first medical device 14A to the second medical device 14B.

An additional or alternative validation of the "right patient" can be accomplished by caregiver visual confirmation of the patient following the auto-association procedure described above in relation to FIG. 21, and is also applicable to the five-rights procedures described above with respect to FIGS. 5, 5A, 6 and 6A. In this process, the patient 110 is photographed with a digital camera (not shown) at the time of admission and the digital photo is stored with the electronic patient record at the HIS 18. When a medication order is requested for a specific patient, the digital photo is sent to the MMU 12 and upon completion of the association process, the digital photo is transmitted from MMU 12 to the medical device 14 at the patient 110 bedside. The image of the patient 110 is sent to the display 88 of the medical device 14, which is preferably a high resolution touch screen at least approximately 12 cm by 12 cm. The image of the patient 110 is then placed on the display 88 and the caregiver 114 is prompted by the display 88 to "Confirm Patient". The caregiver 114 confirms a patient match upon visual comparison of the patient 110 with the image on the display 88.

Alternatively, the digital photo information alternatively can be stored on the indicator 112 or 112A and transmitted by the transmitter/receiver 178 thereof. The digital photo is transmitted to the medical device 14 when the medical device 14 has been associated with the patient 110.

Figure 22:
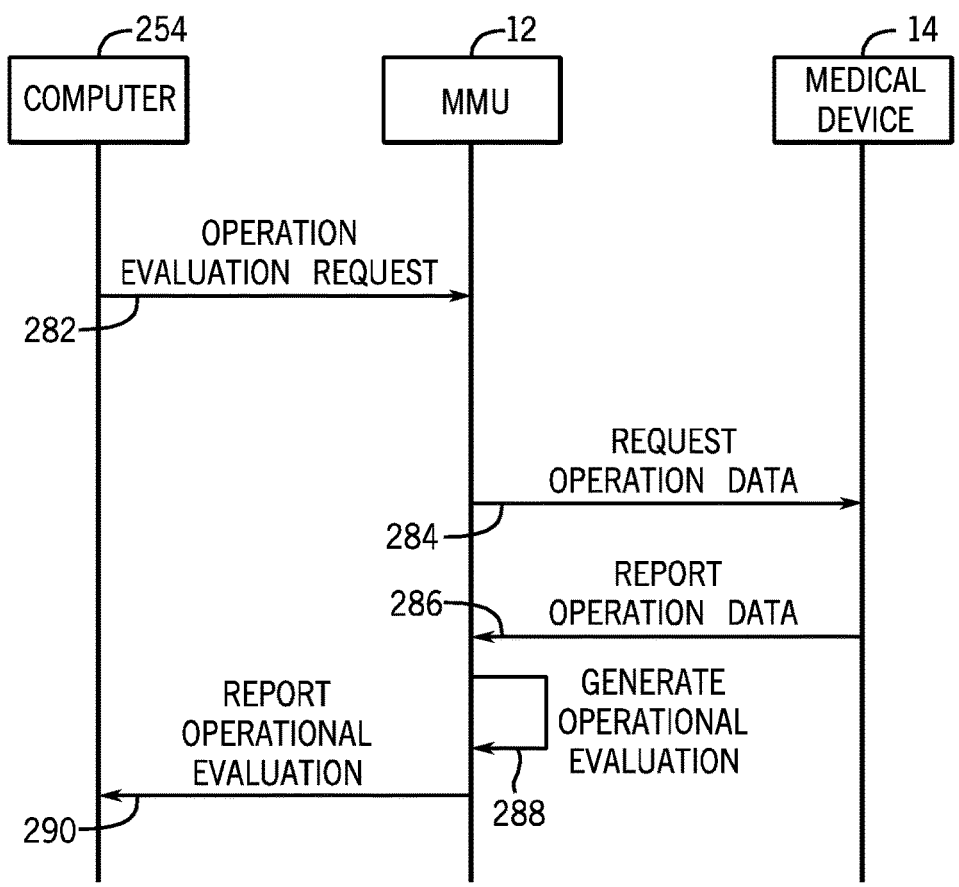
FIG. 22 is a flow chart of the medication management system generating an operation evaluation report of a caregiver or medical device.

With reference to FIG. 22, another portion of the functional steps of the Monitor Pump 52 program in the MMU 12 and the corresponding Monitor Pump 130 program in the medical device 14 are shown in operation with the computer 254. To begin to request a specific evaluation for the operation of a specific medical device 14, or group of medical devices 14, the user 256 (not shown) enters a query for the operation evaluation of a medical device 14. The computer 254 sends an operation evaluation request 282 message to the MMU 12. The MMU 12 in turn sends a request operation data 284 message to the medical device 14. The medical device 14 sends a report operation data 286 message (including but not limited to event logs, settings, CCA and utilization information) back to the MMU 12 at step 286. The MMU 12 processes the report operation data 286 to generate an operational evaluation at step 288. Once the operational evaluation of the medical device 14 is determined by the MMU 12, a report operational evaluation 290 message is sent from the MMU 12 to the computer 254.

Alternatively, the functional steps of the Monitor Pump 44 program in the MMU 12 and the corresponding the Monitor Pump 130 program shown in FIG. 22 can be performed as a series of "push" steps instead of a series of "pull" steps (as shown in FIG. 22). In a "push" embodiment the medical device 14 periodically reports the operation data to the MMU 12. Likewise, the MMU 12 periodically processes the report operation data 286 to generate an operational evaluation at step 288, and periodically reports the operational evaluation of the medical device 14 to the user access device 254 at step 290.

The automated operational evaluation described above, provides a method of evaluating medical device 14 while in operation; thus eliminating the need to postpone evaluation until the medical device 14 is taken out of use. The real-time data collection capabilities of the MMU 12 and Monitor Pump 52 program allow the MMU 12 to determine medical device 14 performance including advanced statistical operations in order to provide quality control data sorting algorithms and aggregation of data and control for a PAN 113 (not shown). For example, consider a MMS 10 where multiple discreet single or multiple channel medical devices 14 (or channels) are connected to a single patient 110 (not shown). The Monitor Pump 52 program collects all medical device 14 information in real-time and then compares medical device 14 statistics to one another. Likewise, infuser channels can be compared to other infuser channels within the same multiple channel medical device or in other devices. Monitor Pump 52 program therefore can detect a "bad actor" if any one of the medical devices 14 or channels is operating at a level statistically lower or higher than the other medical devices 14 or channels. This statistical determination can be made by collecting and comparing the mean and standard deviation of appropriate data elements. This statistical determination can be performed selectably on any of the data that is routinely collected by the medical device 14 event log and any that may be acquired from the instrumentation of the medical device 14. For example, statistical determinations could be performed based on air alarm events, occlusion alarm events, battery usage data, screen response time, etc. MMU 12 then sends the operational evaluation message (including any relevant quality control alert) to an appropriate area (including but not limited to the computer 254) in a form that is appropriate for the particular alert (usually including but not limited to graphically or audibly). Additionally, operational evaluation message (including any relevant quality control alert) can be sent to any number of individuals including but not limited to the caregiver, a biomedical engineer, caregiver supervisor, and a doctor.

With reference to FIG. 17, the medical device 14 is designed as a multi-processor, where many features are not hardwired, but instead can be uniquely configured based on rules, the location of the medical device 14, etc. For example, the medical device 14 is designed to allow a customized display based on the Clinical Care Area (CCA) 253A or 253B the medical device 14 is located in and/or assigned too. An example of this would be the MMU 12 instructing the medical device 14 to have a display of a particular color or warning tones/volumes based on the location of the medical device 14 in the hospital, time of day, caregiver information, patient information, or the type of medication being supplied. For example, the patient information could include a patient diagnosis and/or a disease state. For example, alarm volumes and display brightness can be set lower in the pediatric clinical care area or at night than in the emergency room clinical care area or during the daytime.

With reference to FIG. 4, similarly, the medical device 14 is designed to allow a customized display based on user information supplied to the medical device 14 (from the MMU 12 for example). Such user based customized display could include changes in language preference, limited access depending on the security level of the caregiver 114, customizing the displayed information based on the training level of the individual or recent interactions therewith, and/or customizing an automated help function based on training level of the user or recent interactions therewith. The MMU 12 presents a user with a default view based on the user's role. The MMU 12 permits a default view for each role to be configurable in terms of the data detail presented. The MMU 12 allows a user with the appropriate privilege to set a particular presented view as the preferred or default starting view for that user following login. The MMU 12 allows a user to access databases and details based on role and privilege. The MMU 12 allows a user to access other views based on role and privilege. Each presented view includes: a common means of navigating among views, both summary and detail, access to privacy, security, and other policy statements, access to online help, and a logoff capability. Additionally, an emergency bypass (such as a passcode) would be provided to bypass security restrictions in case of an emergency.

With reference to FIG. 22, another portion of the functional steps of the Monitor Pump 52 program in the MMU 12 and the corresponding Monitor Pump 130 program in the medical device 14 are shown in operation with the computer 254. The MMU 12 tracks and records actions taken by the caregiver 114 based on operational data reported from one or more medical devices 14. Just as the MMU 12 is capable of generating an operational evaluation of each medical device 14, the MMU 12 can likewise generating an operational evaluation of each caregiver 114 (not shown) at step 288. This operational evaluation of each caregiver 114 includes records of each caregiver's 114 actions (or, in some cases, inactions), sorting of these actions based on given criteria, and tracking of any trends in these actions. In general, these records of actions include any task lists, medication administration records, treatments, and other actions associated with the caregiver's 114 responsibilities. Such records of actions may combine medications administered, treatments, and other actions for multiple patients under the care of an individual caregiver. MMU 12 then sends the operational evaluation message (including any relevant quality control alert) to an appropriate area (e.g. to the computer 254 or caregiver supervisor's computer (not shown)) in a form that is appropriate for the particular alert (usually including but not limited to graphically or audibly). Additionally, operational evaluation message (including any relevant quality control alert) can be sent to any number of individuals including but not limited to the caregiver, a biomedical engineer, caregiver supervisor, and a doctor.

Additionally, the MMU 12 can instruct the medical device 14 to customized display 88 based on the operational evaluation message. Thus, the display 88 is adjusted by the MMU 12 based a determination that the caregiver 114 requires additional or different information displayed to improve caregiver 114 interaction with the medical device 14. For example, detailed step by step instructions can be placed on display 88, where the MMU 12 recognizes a caregiver 114 who is not familiar with a particular therapy, using the display 88 as the instruction means. Likewise, where the MMU 12 recognizes that a caregiver 114 has limited experience programming the medical device 14 (caregiver experience) or in previous interactions had made errors programming a particular function (caregiver error rate) or was a statistically longer than the norm at programming a particular function (caregiver response time), the MMU 12 instructs the medical device 14 to display pertinent training information.

In another embodiment best understood with reference to FIG. 4A, the medical device 14 is designed to act as a web server for the input device 32 or other similar devices within proximity to the medical device 14. In this embodiment, medical device 14 is equipped to supply the input device 32 web browser with medical device related information as well as non-medical device related information such as task lists, etc. Additionally, the medical device 14 displays a dual function screen having both a pump monitor screen portion and a web browser screen portion. Further, supplying the medical device 14 as a web server permits a remote web browser to associate with the medical device 14 to configure the medical device 14 or run diagnostics on the medical device 14.

With reference to FIGS. 2 and 4A, another portion of the Monitor Pump 52 program in the MMU 12 and the corresponding Monitor Pump 130 program in the medical device 14 is directed to cloning between medical devices 14. The medical devices 14 are designed to have wireless data sharing between each medical device 14 sufficient to permit cloning of all patient information between each medical device 14, and/or the multi-sequencing of a set of medical devices 14 without a hardwired connection. The MMU 12 adjudicates this cloning and/or multi-sequencing.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A system for configuring an infusion pump, the system comprising:
   an infusion pump configured to deliver medication to a patient, the infusion pump including
     (i) a first memory storing program instructions,
     (ii) a first processor communicating with the memory to execute the program instructions to perform functions of the infusion pump, and (iii) a first network interface in communication with the first processor and configured to receive input for pump configuration of the infusion pump over an internal wireless network;

a display coupled to the infusion pump; and an input device in communication with the infusion pump over the internal wireless network via the first network interface;

wherein the input device is configured to operate as a local web server over the internal wireless network to configure network properties of the infusion pump over the internal wireless network, wherein the pump configuration of the infusion pump comprises updating drug library and infusion pump software; and wherein the configuration of network properties enable a remote web browsing system to associate directly with the infusion pump to update the pump configuration.

2. The system of claim 1, wherein the input device further comprises a barcode scanner configured to scan an identification tag associated with the infusion pump and wherein the input device is configured to automatically associate the infusion pump with identification data included in the identification tag based on the scanning.

3. The system of claim 2, wherein the identification tag comprises medical device identification (ID).

4. The system of claim 2, wherein the identification tag comprises patient ID.

5. The system of claim 2, wherein the identification tag comprises caregiver ID.

6. The system of claim 2, wherein the drug library is updated based on the identification tag.

* * * * *